US 011704142B2

(12) United States Patent
Morrise

(10) Patent No.: US 11,704,142 B2
(45) Date of Patent: Jul. 18, 2023

(54) COMPUTER APPLICATION WITH BUILT IN TRAINING CAPABILITY

(71) Applicant: yoR Labs, Inc., Portland, OR (US)

(72) Inventor: Matthew C. Morrise, Portland, OR (US)

(73) Assignee: YOR LABS, INC., Beaverton, OR (US)

( * ) Notice: Subject to any disclaimer, the term of this patent is extended or adjusted under 35 U.S.C. 154(b) by 0 days.

(21) Appl. No.: 17/455,586

(22) Filed: Nov. 18, 2021

(65) Prior Publication Data

US 2022/0156094 A1    May 19, 2022

Related U.S. Application Data

(60) Provisional application No. 63/115,873, filed on Nov. 19, 2020.

(51) Int. Cl.
| | |
|---|---|
| *G06F 9/451* | (2018.01) |
| *G06F 3/0482* | (2013.01) |
| *G06F 3/04817* | (2022.01) |
| *G06F 3/04845* | (2022.01) |
| *G16H 30/40* | (2018.01) |
| *G09B 19/00* | (2006.01) |

(52) U.S. Cl.
CPC ............ *G06F 9/453* (2018.02); *G06F 3/0482* (2013.01); *G06F 3/04817* (2013.01); *G06F 3/04845* (2013.01); *G09B 19/003* (2013.01); *G16H 30/40* (2018.01)

(58) Field of Classification Search
None
See application file for complete search history.

(56) References Cited

U.S. PATENT DOCUMENTS

| | | | |
|---|---|---|---|
| 5,617,371 A | 4/1997 | Williams | |
| 5,903,516 A | 5/1999 | Greenleaf et al. | |
| 6,031,529 A * | 2/2000 | Migos | G06F 3/04847 |
| | | | 715/783 |
| 6,063,030 A | 5/2000 | Vara et al. | |
| 6,120,450 A | 9/2000 | Li | |
| 6,607,489 B2 | 8/2003 | Hoctor | |

(Continued)

OTHER PUBLICATIONS

Bradley, "Retrospective Transmit Beamformation", Whitepaper ACUSON SC2000™ Volume Imaging Ultrasounds System, Aug. 2008.

*Primary Examiner* — Ryan Barrett
(74) *Attorney, Agent, or Firm* — Knobbe, Martens, Olson & Bear LLP

(57) ABSTRACT

Systems and methods for providing a built-in training capability for a computer application associated with multiple operations. A control icon may be presented along with an image associated with the particular computer application. The control icon may list training tasks that are associated with the particular computer application or the particular image and train a user in performing a particular operation. Based upon a user interaction with the control icon, a training task may be implemented. The training task may comprise multiple steps or actions required to complete the task. The training task may cause a written description of each action and a training icon to be presented to the user. The training task may therefore assist the user in performing the operation associated with the training task.

20 Claims, 19 Drawing Sheets

(56) References Cited

U.S. PATENT DOCUMENTS

| | | |
|---|---|---|
| 7,423,578 B1 | 9/2008 | Tietjen |
| 7,667,639 B2 | 2/2010 | Cheng et al. |
| 7,750,849 B2 | 7/2010 | Hjelmstad |
| 8,517,946 B2 | 8/2013 | Kim |
| 9,030,354 B2 | 5/2015 | Natarajan |
| 9,132,913 B1 | 9/2015 | Shapiro et al. |
| 9,323,445 B2 | 4/2016 | Kritt et al. |
| 9,342,156 B2 | 5/2016 | Huh |
| 9,986,969 B2 | 6/2018 | Call et al. |
| 10,401,492 B2 | 9/2019 | Brooks |
| 10,624,612 B2 | 4/2020 | Sumi |
| 2002/0173721 A1 | 11/2002 | Grunwald |
| 2002/0173722 A1 | 11/2002 | Hoctor et al. |
| 2003/0055334 A1 | 3/2003 | Steinbacher et al. |
| 2004/0102700 A1 | 5/2004 | Asafusa |
| 2007/0027733 A1* | 2/2007 | Bolle ............... G06Q 10/0639 705/7.13 |
| 2007/0174772 A1* | 7/2007 | Gorman ............... G10L 13/00 707/E17.102 |
| 2007/0200760 A1 | 8/2007 | Hjelmstad |
| 2007/0239001 A1 | 10/2007 | Mehi et al. |
| 2007/0259158 A1 | 11/2007 | Friedman et al. |
| 2008/0012753 A1 | 1/2008 | Cheng |
| 2008/0114239 A1 | 5/2008 | Randall et al. |
| 2008/0306385 A1 | 12/2008 | Jago |
| 2009/0271704 A1* | 10/2009 | Cohen ............... G06F 3/0481 715/779 |
| 2010/0030076 A1 | 2/2010 | Vortman et al. |
| 2010/0146431 A1* | 6/2010 | Raji ............... G06F 3/0481 715/781 |
| 2010/0160784 A1 | 6/2010 | Poland |
| 2010/0251823 A1 | 10/2010 | Adachi |
| 2011/0077524 A1 | 3/2011 | Oshiki et al. |
| 2011/0208052 A1 | 8/2011 | Entrekin |
| 2012/0075208 A1* | 3/2012 | Tamiya ............... G06F 9/453 345/173 |
| 2012/0157851 A1 | 6/2012 | Zwirn |
| 2013/0227052 A1 | 8/2013 | Wenzel |
| 2013/0234891 A1 | 9/2013 | Natarajan et al. |
| 2013/0238990 A1* | 9/2013 | Ubillos ............... G06F 16/54 715/708 |
| 2013/0253317 A1 | 9/2013 | Gauthier |
| 2014/0035916 A1 | 2/2014 | Murphy |
| 2014/0046188 A1 | 2/2014 | Yen et al. |
| 2014/0058266 A1 | 2/2014 | Call et al. |
| 2014/0087342 A1* | 3/2014 | Campanatti, Jr. ...... G09B 23/00 434/262 |
| 2014/0164965 A1 | 6/2014 | Lee et al. |
| 2014/0219059 A1 | 8/2014 | Younghouse |
| 2015/0019488 A1* | 1/2015 | Higginson ............ G06F 16/214 707/634 |
| 2015/0082251 A1* | 3/2015 | Lam ............... G06F 16/955 715/843 |
| 2015/0293223 A1 | 10/2015 | Park et al. |
| 2016/0161589 A1 | 6/2016 | Benattar |
| 2016/0161594 A1 | 6/2016 | Benattar |
| 2016/0161595 A1 | 6/2016 | Benattar |
| 2016/0165338 A1 | 6/2016 | Benattar |
| 2016/0165341 A1 | 6/2016 | Benattar |
| 2017/0090571 A1 | 3/2017 | Bjaerum |
| 2017/0307755 A1 | 10/2017 | Brooks |
| 2017/0343668 A1 | 11/2017 | Brooks et al. |
| 2018/0000453 A1 | 1/2018 | Hunter et al. |
| 2018/0055483 A1 | 3/2018 | Hunter |
| 2019/0324139 A1 | 10/2019 | Brooks |
| 2019/0353975 A1 | 11/2019 | DiDomenico |
| 2020/0046321 A1* | 2/2020 | Duda ............... A61B 8/461 |

* cited by examiner

FIG. 14

COMPUTER APPLICATION WITH BUILT IN TRAINING CAPABILITY

BACKGROUND OF THE INVENTION

Field

This disclosure relates to built-in assistance capabilities for computer applications. Specifically, this disclosure relates to the determination of steps that are associated with a task and guiding a user to perform each step of the task based on interactions of the user with a user interface.

Description of the Related Art

Help documentation is used to assist users of a computer application. A user can interact with the computer application in order to perform numerous procedures. The computer applications and the procedures commonly have various nuances specific to the particular application and procedure. For example, one interaction may correspond to one procedure in a first computer application and a second procedure in a second computer application. The computer application can offer help documentation described to a user how to perform an operation with the application. The user can parse the documentation to determine information associated with the procedure they want to perform.

Numerous procedures may be used by a user to interact with the computer application. The computer application may cause an image to be presented to the user via a user interface. The display of the image may be adjusted using various controls on a user interface, for example, the image may be adjusted via zooming or panning the image. The controls for adjusting the image may be located at different locations on the user interface. Further, different adjustments may correspond to different controls or different combinations of controls. It would be advantageous to be able to be able to provide training capabilities for presenting steps for these procedures and indicate how the steps can be taken by the user. Also, it would be advantageous to provide text or feedback that enables a user to determine how to perform the various steps that should be taken in order to effectuate a desired action.

SUMMARY

Provided herein is a system and method for presenting steps for executing a given procedure on a user interface, the steps presented with text and graphical feedback, displayed in an image on the user interface, using a training icon on the user interface. One innovation includes a system comprising a first non-transitory computer storage medium configured to store an image, a second non-transitory computer storage medium configured to at least store computer-executable instructions, and one or more computer hardware processors in communication with the second non-transitory computer storage medium, the one or more computer hardware processors configured to execute the computer-executable instructions to at least: cause display of the image on a user interface of a display device, cause display of a control icon on the user interface, receive a user interaction, wherein the user interaction corresponds to an interaction by a user with the control icon, wherein the user interaction comprises a selection of a training task by the user, based at least in part on receiving the user interaction, determine a training task, and cause display of a training icon corresponding to a first action associated with the training task.

Various embodiments of the system may include one or more other features, or different features. For example, wherein the one or more computer hardware processors are further configured to execute the computer-executable instructions to: receive a second user interaction, wherein the second user interaction corresponds to a second interaction by the user with the training icon, wherein the second user interaction corresponds to the first action, determine that the user completed the first action based at least in part on receiving the second user interaction; and, based at least in part on determining that the user completed the first action, cause display of a second training icon, the second training icon corresponding to a second action associated with the training task. In some embodiments, the training task comprises one or more actions, the one or more actions including the first action. In some embodiments, the one or more computer hardware processors are further configured to execute the computer-executable instructions to: cause display of a second image on the user interface, cause display of a second control icon on the user interface, receive a second user interaction, wherein the second user interaction corresponds to a second interaction by a user with the second control icon, wherein the second user interaction comprises a selection of a second training task by the user, based at least in part on receiving the second user interaction, determine a second training task, and cause display of a second training icon corresponding to a first action associated with the second training task. In some embodiments, the second control icon and the control icon are different control icons. In some embodiments, the second training task and the training task are different training tasks. In some embodiments, the second image and the image are different images, wherein the second training task and the training task are the same training task. In some embodiments, the image is an ultrasound image.

Other embodiments of such systems can include other features. For example, in some embodiments, the one or more computer hardware processors are further configured to execute the computer-executable instructions to cause display a title associated with the training task. In some embodiments, the one or more computer hardware processors are further configured to execute the computer-executable instructions to cause display a title associated with the first action. In some embodiments, the training task comprises a training to, one or more of: freeze the image, save the image, adjust a contrast of the image, adjust a time gain compensation, zoom, pan, draw an ellipse on the image, or change a scanning depth. In some embodiments, causing display of the training icon comprises causing display of the training icon in a location associated with the first action. In some embodiments, the training icon is an arrow. In some embodiments, the training icon designates the first action. In some embodiments, the training icon represents the first action. In some embodiments, the one or more computer hardware processors are further configured to execute the computer-executable instructions to cause display of training text with the training icon, the training text designating a manner of executing the first action. In some embodiments, one or more of the training icon or the control icon comprise a first color and the image comprises a second color. In some embodiments, the one or more computer hardware processors are further configured to execute the computer-executable instructions to increase a size of one or more of the training icon or the control icon. In some embodiments, the one or more computer hardware processors are further configured to execute the computer-executable instructions to receive a second user interaction, wherein the second user interaction corresponds to an interaction by the user with the training icon. In some embodiments, the one or more computer hardware processors are further configured to execute the computer-executable instructions to, based at least in part on the second user interaction, determine that the first action is complete. In some embodiments, the one or more computer hardware processors are further configured to execute the computer-executable instructions to receive a second user interaction, wherein the second user interaction corresponds to an interaction by the user with the image. In some embodiments, the one or more computer hardware processors are further configured to execute the computer-executable instructions to, based at least in part on the second user interaction, determine that the first action is complete. In some embodiments, the one or more computer hardware processors are further configured to execute the computer-executable instructions to, based at least in part on determining that the first action is complete, cause display of a second training icon. In some embodiments, the one or more computer hardware processors are further configured to execute the computer-executable instructions to, based at least in part on determining that the first action is complete, modify the training icon to indicate that the first action is complete. In some embodiments, the one or more computer hardware processors are further configured to execute the computer-executable instructions to cause display of a third training icon, wherein a user interaction with the third training icon causes display of the first training icon. In some embodiments, the third training icon comprises an arrow.

Other embodiments of such systems can include other features. For example, in some embodiments, the one or more computer hardware processors are further configured to execute the computer-executable instructions to determine that the first action is not complete. In some embodiments, the one or more computer hardware processors are further configured to execute the computer-executable instructions to, based at least in part on determining that the first action is not complete, cause display of the first training icon. In some embodiments, the one or more computer hardware processors are further configured to execute the computer-executable instructions to, based at least in part on determining that the first action is not complete, cause display of a prompt for the user to skip the first action. In some embodiments, the one or more computer hardware processors are further configured to execute the computer-executable instructions to, based at least in part on determining that the first action is not complete, cause display of a prompt for the user to complete the first action. In some embodiments, the training icon comprises one or more steps. In some embodiments, the one or more computer hardware processors are further configured to execute the computer-executable instructions to cause display of an animation between the one or more steps. In some embodiments, the one or more computer hardware processors are further configured to execute the computer-executable instructions to cause display of a training menu based at least in part on the user interaction, wherein the training menu includes a plurality of training tasks, the plurality of training tasks including the training task. In some embodiments, the training menu includes a disablement option, wherein an interaction with the disablement option disables the training icon. In some embodiments, the training menu includes a re-enablement option, wherein an interaction with the re-enablement option re-enables the training icon. In some embodiments, to select the training task, the user interacts with the training menu.

Another innovation includes a method of providing a system for training a user. In some embodiments of such methods, causing display of an image on a user interface of a display device, causing display of a control icon on the user interface, receiving a user interaction, wherein the user interaction corresponds to an interaction by a user with the control icon, wherein the user interaction comprises a selection of a training task by the user, based at least in part on receiving the user interaction, determining a training task, and causing display of a training icon corresponding to a first action associated with the training task. Embodiments of such methods can include additional features. For example, the method can further include receiving a second user interaction, wherein the second user interaction corresponds to a second interaction by the user with the training icon, wherein the second user interaction corresponds to the first action, determining that the user completed the first action based at least in part on receiving the second user interaction, and based at least in part on determining that the user completed the first action, causing display of a second training icon, the second training icon corresponding to a second action associated with the training task. In some embodiments, the training task comprises one or more actions, the one or more actions including the first action. The method can further include causing display of a second image on the user interface, causing display of a second control icon on the user interface, receiving a second user interaction, wherein the second user interaction corresponds to a second interaction by a user with the second control icon, wherein the second user interaction comprises a selection of a second training task by the user, based at least in part on receiving the second user interaction, determining a second training task, and causing display of a second training icon corresponding to a first action associated with the second training task.

In some embodiments of providing a system for training a user, the second control icon and the control icon are different control icons. In some embodiments, the second training task and the training task are different training tasks. In some embodiments, the second image and the image are different images, wherein the second training task and the training task are the same training task. In some embodiments, the image is an ultrasound image. The method can further include causing display of a title associated with the training task. The method can further include causing display of a title associated with the first action. In some embodiments, the training task comprises a training to, one or more of: freeze the image, save the image, adjust a contrast of the image, adjust a time gain compensation, zoom, pan, draw an ellipse on the image, or change a scanning depth. In some embodiments, causing display of the training icon comprises causing display of the training icon in a location associated with the first action. In some embodiments, the training icon is an arrow. In some embodiments, the training icon designates the first action. In some embodiments, the training icon represents the first action. The method can further include causing display of training text with the training icon, the training text designating a manner of executing the first action. In some embodiments, one or more of the training icon or the control icon are associated with a first color and the image is associated with a second color. The method can further include increasing a size of one or more of the training icon or the control icon. The method can further include receiving a second user interaction, wherein the second user interaction corresponds to an interaction by the user with the training icon. The method can further include, based at least in part on the second user interaction, determining that the first action is complete. The method can further include receiving a second user interaction, wherein the second user interaction corresponds to an interaction by the user with the image. The method can further include, based at least in part on the second user interaction, determining that the first action is complete. The method can further include, based at least in part on determining that the first action is complete, causing display of a second training icon. The method can further include, based at least in part on determining that the first action is complete, modifying the training icon to indicate that the first action is complete. The method can further include causing display of a third training icon, wherein a third user interaction with the third training icon causes display of the first training icon. In some embodiments, the third training icon comprises an arrow.

In some embodiments of providing a system for training a user, the method can further include determining that the first action is not complete. The method can further include, based at least in part on determining that the first action is not complete, causing display of the first training icon. The method can further include, based at least in part on determining that the first action is not complete, causing display of a prompt for the user to skip the first action. The method can further include, based at least in part on determining that the first action is not complete, causing display of a prompt for the user to complete the first action. In some embodiments, the training icon comprises one or more steps. The method can further include causing display of an animation between the one or more steps. The method can further include causing display of a training menu based at least in part on the user interaction, wherein the training menu includes a plurality of training tasks, the plurality of training tasks including the training task. In some embodiments, the training menu includes a disablement option, wherein an interaction with the disablement option disables the training icon. In some embodiments, the training menu includes a re-enablement option, wherein an interaction with the re-enablement option re-enables the training icon. In some embodiments, to select the training task, the user selects the training task by interacting with the training menu.

BRIEF DESCRIPTION OF THE DRAWINGS

FIG. 14 is a further picture of an example user interface, now showing a control icon and a training icon.

DETAILED DESCRIPTION OF CERTAIN INVENTIVE ASPECTS

Overview

Figure 1:
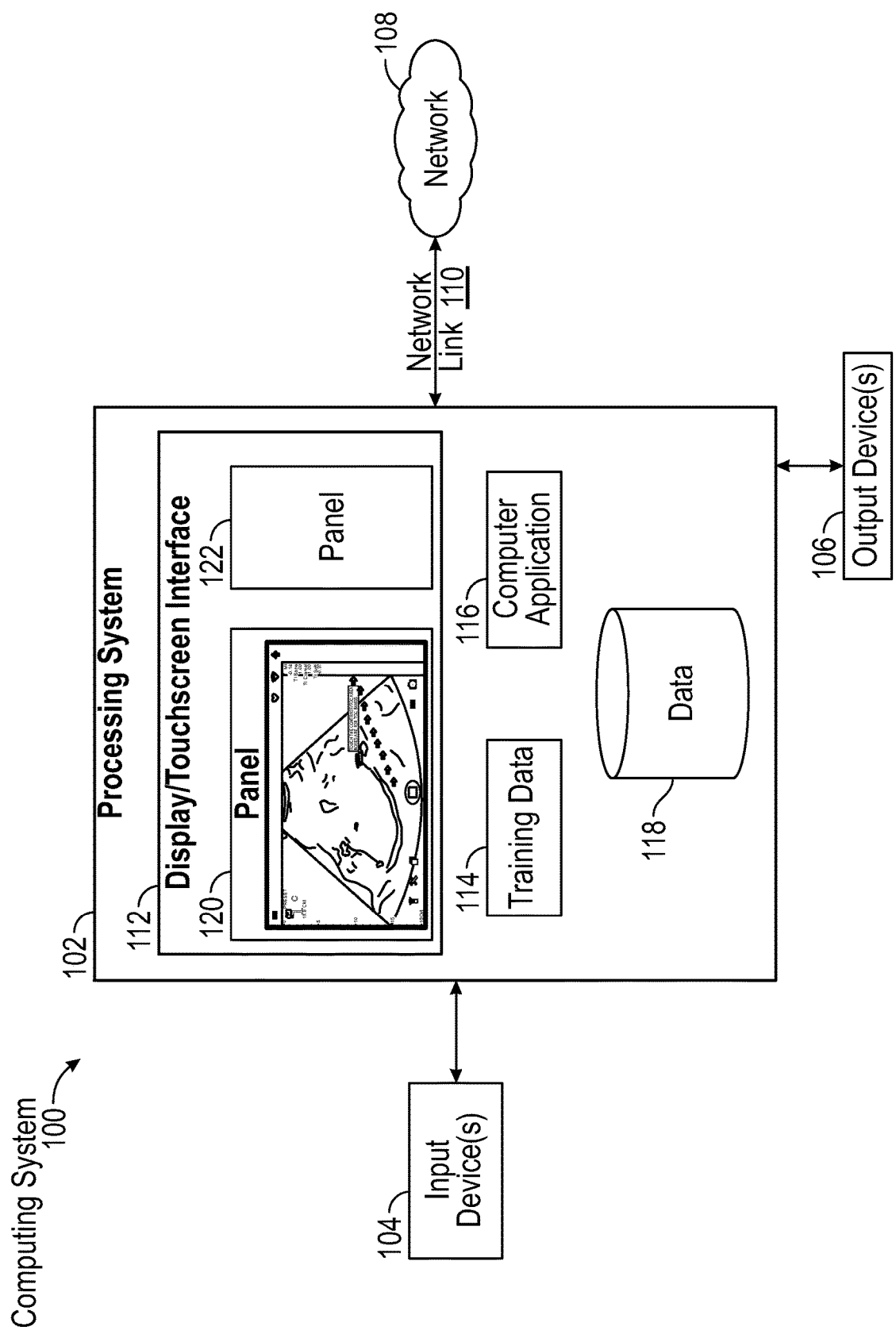
FIG. 1 is a block diagram illustrating an example of an imaging system that can generate and display a user interface configured with a program to provide user assistance (or training) capabilities.

Embodiments of systems and methods for a computer application with a built-in training capability are disclosed herein. A user interface may implement a computer application that causes an image (e.g., a website, an interface, a series of images, a video, or any other visual presentation) to be presented via the user interface. The computer application may cause the image to be presented by the user interface such that the user can interact with the image. The image may include images received over a physical connection, a network connection, or any other connection. For example, the images may include images provided by an HTTP server executing computer code to provide a website to a user. Further, the image may include ultrasound images. The user interface may be configured to receive a series of user interactions from a user and alter the image based on the interactions. The interactions may include adjusting image display parameters for a user to better visually analyze objects in the displayed image. The interactions may include freezing the image, saving the image, adjusting a contrast of the image, adjusting a time gain compensation, zooming, panning, drawing an ellipse on the image, or changing a scanning depth. For example, the user may interact with the user interface in order to pan the image using controls provided by the user interface. Each interaction may be associated with specific controls in order to effectuate the interaction. For example an interaction to zoom in or out of the image may comprise adjusting a zoom button. Further, separate zoom buttons may be provided to zoom into the image and zoom out of the image. Specific combinations of controls may be used for additional interactions. For example, to control contrast and time gain compensation ("TGC") using a unified control, the user interactions for such control may include receiving a first user interaction comprising a selection of a point on the user interface and receiving a second user interaction comprising a dragging of the selection to another point on the user interface. In order to aid the user in interacting with the user interface, the user interface may provide a computer application with built-in training capabilities.

To improve a user's experience with the user interface and to provide more efficient computer applications, a computer application with integrated and interactive assistance capabilities is described herein. As described herein, the user interface can be, or include, a graphical user interface (GUI) that is displayed in one or more panels on a display (e.g., an LED, LCD, or an OLED display). The display may include touchscreen structure incorporated into the display, or over the display, to provide an interface that a user can provide an input or a selection to interact with the user interface by touching, nearly touching, or gesturing, for example using a finger or a stylus. For ease of description, the phrase "user interface" and "display" may be used synonymously herein to refer to the user interface presented on the display. In some cases, the user interface is configured such that it graphically generates and displays steps for a given procedure with information text and graphical feedback relating to the procedure the user wants to perform. One or more images presented by the computer application running on the user interface can include a control icon or a menu option. A selection of the control icon or menu option can provide a context sensitive menu of training tasks. For example, the menu of training tasks may be based on the specific computer application being implemented, the specific procedures currently being implemented by the computer application, the images being presented by the computer application, or the state of the computer application or user interface. In some cases, upon selection of a training task, a title of the task may be displayed on the user interface and a training icon may be provided on the user interface. The training task may correspond to a series of steps or actions that can be represented as a tree of steps. The training icon may be displayed in an area associated with a first step or action of the training task. In some cases, the training icon may be an arrow or an icon representing a required action. In some cases, text may be provided with the training icon indicating a desired action. Further, the training icon may be colored so as to stand out on the user interface. Upon completion of the first step or action, the computer application may recognize the completion of the action and change the training icon. In some cases, the user can interact with the training icon to move to a next step or action. Further, the user can interact with a button to move to a previous step or action. In some cases, a step or action may include multiple sub-steps. The movement between the sub-steps may be animated. In some cases, the training program may determine that a current step or action is not complete and may prompt the user to complete the current step or action before moving to the next step. Upon completion of the final step of the training task, the training program may move the training icon to the control icon or provide another indication that the training task is complete. In some cases, the menu of training tasks can include a disablement option to disable a training mode to remove the control icon or training icon. When the training mode has been disabled, the built-in training capabilities may be disabled. Further, an enablement option can be provided to enable a training mode and the built-in training capabilities.

In light of the description above, it will be understood that the embodiments disclosed herein substantially improve computer capabilities and functionality, e.g., by increasing a user's efficiency and increasing the user's capabilities, and improving the user's knowledge without additional human resources of time or the need to have another person physically present. Specifically, the embodiments disclosed herein enable a system to dynamically improve the functionality of a computing system by providing built-in user assistance capabilities. The ability to provide built-in user assistance capabilities that enables the underlying systems to more efficiently communicate with a user of the computing system, thereby improving the functionality of the computing system. Specifically, the built-in training capabilities can provide a user with a training program that offers multiple tasks that can be presented to walk the user through a corresponding procedure. The multiple tasks can further correspond to different functionalities offered by the computing system. Thus, the presently disclosed embodiments represent an improvement in the functioning of the computing system. Moreover, the presently disclosed embodiments address technical problems inherent within computing systems; specifically, how to assist a user of the computing system in interacting with the user interface. These technical problems are addressed by the various technical solutions described herein, including the inclusion of computer-executable instructions within a computing system that enable the computing system to present built-in training capabilities based on various tasks that a user can perform. Thus, the present application represents a substantial improvement on existing computing system functionality in general.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

"Computer application" in this context refers to an application that is configured to be implemented on a computing device (e.g., a mobile device, a computer, a server, a node, a virtual computing environment) in order to perform a desired set of operations. In some embodiments, the computer application may correspond to software. In other embodiments, the computer application may correspond to hardware. For example, the computer application may be stored and/or implemented by a hard drive, a removable flash drive, a virtualized computing environment, an operating system, a computing device, a compact disc, an instance of the computer application, etc. The computer application can be a mobile application that is implemented by a mobile device. Examples of a computer application may be an application for word processing, gaming, application drafting, ultrasound imaging, condition simulations, product development, presentation, application suites, engineering, multimedia, spreadsheets, etc. Such a computer application can be either be installed locally on a computing device or may be implemented through a network. The computer application can be implemented via a system software such as Windows, Mac, etc. that is configured to run and execute the computer application on a given computing device. In such systems, non-transitory computer mediums are used to store programs that include instructions that cause one or more computer hardware processors to provide the functionality (processes and methods) described herein.

"Module" in this context refers to logic having boundaries defined by function or subroutine calls, branch points, application program interfaces, or other technologies that provide for the partitioning or modularization of particular processing or control functions. Modules are typically combined via their interfaces with other modules to carry out a machine process.

"User" in this context refers to the person interacting with a user interface. In other words, the user is implementing a computer application on a user interface. In some embodiments, a user may be a person performing an ultrasound scan.

"Touch screen" in this context refers to a capacitive or resistive display which responds to direct touch manipulation, either by finger (simple or multi-touch), stylus, or both. The user can use the touch-screen to react to what is displayed and to control how it is displayed. The touchscreen enables the user to interact directly with information displayed rather than using a mouse, touchpad, or other intermediate device (with the exception of a stylus).

"Visual Protocol" in this context refers to a protocol that is displayed on a display screen of a computer system, and that is updated based on a user's interactions. The visual protocol can associate a protocol checklist with a diagram of an image (e.g., a diagram of a scanned body part). The visual protocol can also associate the protocol checklist with a textual list of annotations for the image and a series of thumbnail images (a "gallery"), where each of the thumbnail images is associated with a full-size image that can be enlarged when the thumbnail image is selected. The visual protocol can also associate the protocol checklist with measurements that are to be acquired.

Data Representation

In some embodiments, the data representation of an image caused to be presented by the computer application may be able to represent all the needed fields to both display and to signify the exact display variant that should be used. Additionally, the data format may be flexible enough to allow for transformations to other supported display variants if possible.

The image may represent a single frame, or captures which are collections of images along with other properties. Checking the contents of captures allows for explicitly knowing the exact display variant that should be used. Knowing this type then specifies all actions that can be taken on the capture, as well as directing the display on how it should render the image data.

An image may be a single frame or a single slice. In some embodiments, image data that is saved to the database for an individual image may include the following immutable fields:

(1) Raw pixel data for what was imaged.
(2) Depth details to specify constraint of bottom of image. The depth refers to a 2D image's y-axis which corresponds to how deep the scanner is imaging.
(3) Timestamp to have relative timing information relative to other image data
(4) Relative position data in x, y, and z directions.
(5) Relative angle position data in x, y, and z directions.
(6) Relative slice position and total number of slices for beamformed 3D image if applicable.

Example Processing System with Training Capabilities

FIG. 1 is a block diagram illustrating an example of a computing system ("system") 100 that includes a user assistance capability for a computer application. In an example, the system 100 is an imaging system. The computing system 100 includes a processing system 102. In some embodiments, the processing system 102 may be an ultrasound system. The computing system 100 may further include one or more input device(s) 104, one or more output device(s) 106, and a network 108 that are each in communication with the processing system 102. The processing system 102 can be any computer device (e.g., a desktop computer, a tablet, a laptop, a mobile device, a server, a virtualized computing environment, etc.) that is suitably configured to implement computer applications (e.g., perform visual protocols).

The input device(s) 104 may include one or more devices that provide input to the processing system 102. For example, the input device(s) 104 may include one or more computing devices, keyboards, pointing devices (e.g., a mouse, joystick, track-ball, etc.), ultrasound probes, or other devices that are configured to provide information (e.g., images, signals, data, etc.) to the system 100. In the event that the input device(s) 104 includes an ultrasound probe, the ultrasound probe can be a handheld ultrasound device that comprises a transducer array configured to transmit an ultrasound signal to a target object, receive an ultrasound echo signal reflected from the target object, and form ultrasound data corresponding to the target object. The input device(s) 104 may provide input to the processing system 102 via one or more signals. The one or more signals can correspond to one or more instructions for the processing system 102. Further, the input device(s) 104 can be controlled by the processing system 102 to provide data (e.g., ultrasound images) to the processing system 102. In some embodiments, the processing system 102 may be used to view stored data, either locally stored data or remotely stored data, and the input device(s) 104 may not provide data to the processing system 102. In some embodiments, the processing system 102 may not include input device(s) 104. Therefore, the input device(s) can be in communication with the processing system 102 in order to provide instructions or commands to the processing system 102.

As noted above, the computing system 100 may include one or more input device(s) 104. Further, the computing system 100 may include one or more output device(s) 106. The one or more output device(s) 106 can provide an output of the processing system 102. The output device(s) can be one or more devices configured to receive a data signal from the processing system 102. For example, the output device(s) may be one or more of a display, a monitor, a detector, speaker, or any other device capable of receiving a data signal from the processing system 102. In some embodiments, the output device(s) provide further training capabilities. For example, the output device(s) may include a speaker and the speaker may provide audio prompts to a user (e.g., click on a particular box and drag the particular box to certain location). Further, the output device(s) can provide confirmation that the user has successfully or unsuccessfully completed an action or a training task. Therefore, the output device(s) 106 may receive an output from the processing system 102.

As noted above, the computing system 100 may be in communication with one or more input device(s) 104 and/or one or more output device(s) 106. The computing system 100 may be in direct communication (e.g., a local communication) or remote communication (e.g., Bluetooth, WiFi, or any other communication over a network). The processing system 102 may further include a network link 110 for access to a network 108. In some embodiments, the network may be a wide area network, a global area network (e.g., the internet), etc. The processing system 102 may be in communication with network hosts, network devices, servers, etc. via the network 108. The network hosts may represent computing devices operating within the network and may be or may represent physical or logical devices. In some embodiments, the processing system 102 may be in communication with a server (e.g., an http server) and may receive information from the server that the processing system 102 can use to provide an image (e.g., a website or webpage) to the user. The network 108 may be logically implemented by a physical network referred to as a substrate which may include physical network hardware such as routers, switches, network address translators, etc. Therefore, the processing system may include a network link 110 in order to transmit data to a network 108 and the network 108 may further be used to route the data to a destination such as a computing device.

In the example illustrated in FIG. 1, the processing system 102 includes a display and a touchscreen interface. In other examples, the processing system 102 can include a display that without a touchscreen interface. In either example, a user interface can be generated and presented on the display. For clarity of description, the phrase "interface 112" is used herein as referring to a user interface presented on a (touchscreen or non-touchscreen) display, including the display/touchscreen interface illustrated in FIG. 1. The user interface 112 is configured to present one or more images and information related to the images, the procedure being performed, and other information to assist the user, including displaying information (e.g., text, images, symbols and other indicia) to assist the user for a process. For example, the interface 112 may provide a webpage or website (or a representation of a webpage or a website to a user). Further, the interface 112 may provide an image associated with a computer application 116 to a user. For example, a computer application 116 may correspond to ultrasounds and may cause the interface 112 to display ultrasound images, image display information, measurement information, and other information related to an ultrasound imaging. The interface 112 may further include one or more panels 120, 122 to display images provided or associated with the computer application 116. In the example of FIG. 1, the interface 112 is displaying ultrasound image on panel 120 and a blank image on panel 122. It will be understood that any number of panels may be used and in some instances, certain panels may be included in the interface 112, but may not be used. In some preferred embodiments, the interface 112 includes both a display and a touchscreen that are implemented together such that most, or all, of the controls are available on the interface 112. Some embodiments of systems, however, may include an interface 112 that has a separate display and a separate user interface. The interface 112 can be any type of a flat screen, LED screen, electroluminescent display, organic LED, LCD, virtual display and the like that can display information and receive input from a user in the directly to the display or to another device that is in communication with the display. The processing system 102 may also include voice recognition to manipulate information and/or images on the interface 112. The processing system 102 may further include one or more input device(s) 104 and/or output device(s) that can receive information and provide information to the interface 112. Therefore, the interface 112 may provide one or more images that may be modified based on user input.

The interface 112 may present information in a variety of ways. In some embodiments, the interface 112 is divided into a plurality of panels (or sectors) 120, 122, etc. that each may display different information. The information displayed in a given panel may be based on the specific computer application 116 that is being run by the processing system 102. For example, a computer application 116 may cause a first image to be displayed on the panel 120 and a second image on the panel 122. Each image may correspond to different training tasks and the processing system 102 may make different training tasks available for each. In some embodiments, the panels 120, 122 may offer ultrasound imaging information such as one or more of: patient information, an active ultrasound image being currently acquired from a machine transformation of an ultrasound reading in process (active scan), and image display controls. As described in more detail in reference to FIG. 2, the interface 112 can display information related to controlling the display of an ultrasound image, and receive user input via its touchscreen functionality, and/or other input device(s) 104 (e.g., keyboard, mouse, and the like) that are in communication with the processing system 102.

In order to perform certain operations on the image(s) being displayed in the panels 120, 122, the user may interact with various controls in order to perform the operations. These operations may be performed by an interaction with an input device 104 or the interface 112. For example, the operations may be performed by a click, a swipe, a touch, dragging, dropping, making eye contact with, orally instructing, or otherwise interacting with an input device 104 or the interface 112. Operations may further be performed by a specific combination of interactions such as dragging and dropping an icon. The operations may include operations such as zooming, panning, freezing an image, adjusting a contrast, adjusting a time gain compensation, saving an image, drawing on an image, changing the depth of an image, or any other operation performed by controls or interactions. In some embodiments, where the processing system 102 is analyzing an ultrasound image, the operations may include selecting an ultrasound procedure to perform, associating ultrasound images with a patient, and receiving ultrasound images from an input device 104 (e.g., an ultrasound probe). Implementing the computer application may also include recording, associating, measuring comparing, labeling, reporting and/or documenting information received from an input device 104 (e.g., an ultrasound probe).

As mentioned above, the interface 112 may be a combination display and touch screen that allows the user to manipulate the images on the display. Touch-screen based computers comprise computer assemblies combining an internal computer processor and touch sensitive digital display screen. The display and the computer's ability to monitor the positions and motions of finger touches on the touch-screen are coordinated such that finger contact locations can be correlated by the computer with the information displayed at those locations. A variety of gestures may be used to interact with the interface 112, including, but not limited to, touching, swiping, double tap, multiple finger taps, pinch, multi-touch, radio buttons and the like. A processor is coupled to the touch-screen for detecting a touch by the user on the touch-screen that identifies a selected activation area. The processor then performs the device function associated with the stored image manipulation function thereby activating the selected activation area. In some embodiments, the user may interact with the interface 112 through voice recognition, a stylus, keyboard, mouse, virtual reality headset, hand gestures in the air, any other way generally used to interact with a user interface, or a combination thereof. In some embodiments, controls on the input device(s) 104 may be used to input information onto the interface 112.

As noted above, different operations may be performed on the image(s) being displayed in the panels 120, 122, the panels 120, 122 on the interface 112 may further display controls for the user interactions with the images (e.g., interacting with one or more ultrasound images, graphical representations, and measurement of objects depicted in ultrasound images). The processing system 102 may include various modules to facilitate the completion of an operation, for example, the processing system 102 may include a unified contrast and TGC control bar activated by the user interface. The processing system 102 may further include modules such as a camera button to take a picture or record video, a zoom button, a pan button, a save button, a depth button, a drawing button, etc. Each of these modules may require certain interactions in order to perform the desired operations. The modules may be represented on the interface 112. The interface 112 can be divided into a plurality of control panels including, but not limited to, a proportionate graphical representation, a scale or other measuring apparatus, a track pad, a series of one or more virtual controls such as buttons or radio buttons, word bank, structured label bank, tabbed drop down menus, virtual keyboard, active images, virtual trackpad, virtual depth and focus sliders, virtual cine slider, and virtual time gain compensation sliders. In some embodiments, the number and arrangement of control panels may be altered to suit the needs of the user. For example, during a scan, it may be desirable to have an extended display of one or more of the control panels. In some embodiments, there may be one control panels. In other embodiments, there may be 2, 3, 4, 5, 6, 7, 8, 9, 10, or more control panels. Activation of each panel on the interface 112 may perform a function on the interface 112 and can manipulate information on the interface 112.

The processing system 102 may store information that is used to implement the computer application. For example, the processing system 102 may store data 118 that is to be presented on the interface 112 and/or is received by the processing system 102. The processing system 102 may store further information such as images, user information (e.g., patient information), image adjustment information (e.g., image processing information), other imaging data (scans, scan maps, etc.), visual protocols, etc. The data 118 (and other stored information) may be stored in one or more data stores local or remote to the processing system 102 via the network link 110 and the network 108. For example, because of the potentially large size of the data that may be collected for presentation on the interface 112, the data may be stored on a high-speed computer storage device is in communication with the processing system 102 via the network link 110 and the network 108.

The processing system 102 may further store a computer application 116. The computer application 116 can correspond to virtual or physical software that, when implemented by the processing system 102, cause certain applications to be run or presented on the display/touchscreen interface. In some embodiments, the computer application 116 may correspond to hardware. The computer application 116 may further cause an application or program to run on the processing system 102, the computer application 116 may receive input via the input device(s) and/or the interface 112. Further, the computer application 116 may cause certain operations to be performed, as previously mentioned, based on the input. For example, the computer application 116 may correspond to an ultrasound imaging application. A user may perform an interaction such as a click of a mouse via an input device 104, and the computer application 116 may cause the interface 112 to present a zoomed in portion of the ultrasound image. Each computer application may correspond to different functionality and different operations. For example, an ultrasound imaging computer application may offer different operations than a tax return computer application. As the number of computer applications may be vast, it may be advantageous to provide built-in training capabilities that train the user to perform certain operations via the computer application 116.

The built-in training capabilities may be implemented on the interface 112 as a training application (not shown in FIG. 1). In some embodiments, the built-in training capabilities may be part of the computer application 116 or the data 118. The training application may cause a training menu, icon, interface, etc. to be presented by the interface 112. The training menu may include various training tasks that may train a user to perform various operations. The training tasks, and operations, may correspond to and depend on the specific computer application being run. In some embodiments, some training tasks, and operations, may be general such as saving an image or document. The various training tasks may be stored as training data 114 by the computer. The processing system 102 may receive the training data from the computer application 116. In some embodiments, the processing system 102 may receive the training data via the network link 110 and the network 108. Therefore, the training application and the training data 114 may enable a built-in training capability of the processing system 102.

Example Training Capabilities for an Ultrasound Imaging Computer Application

Figure 2:
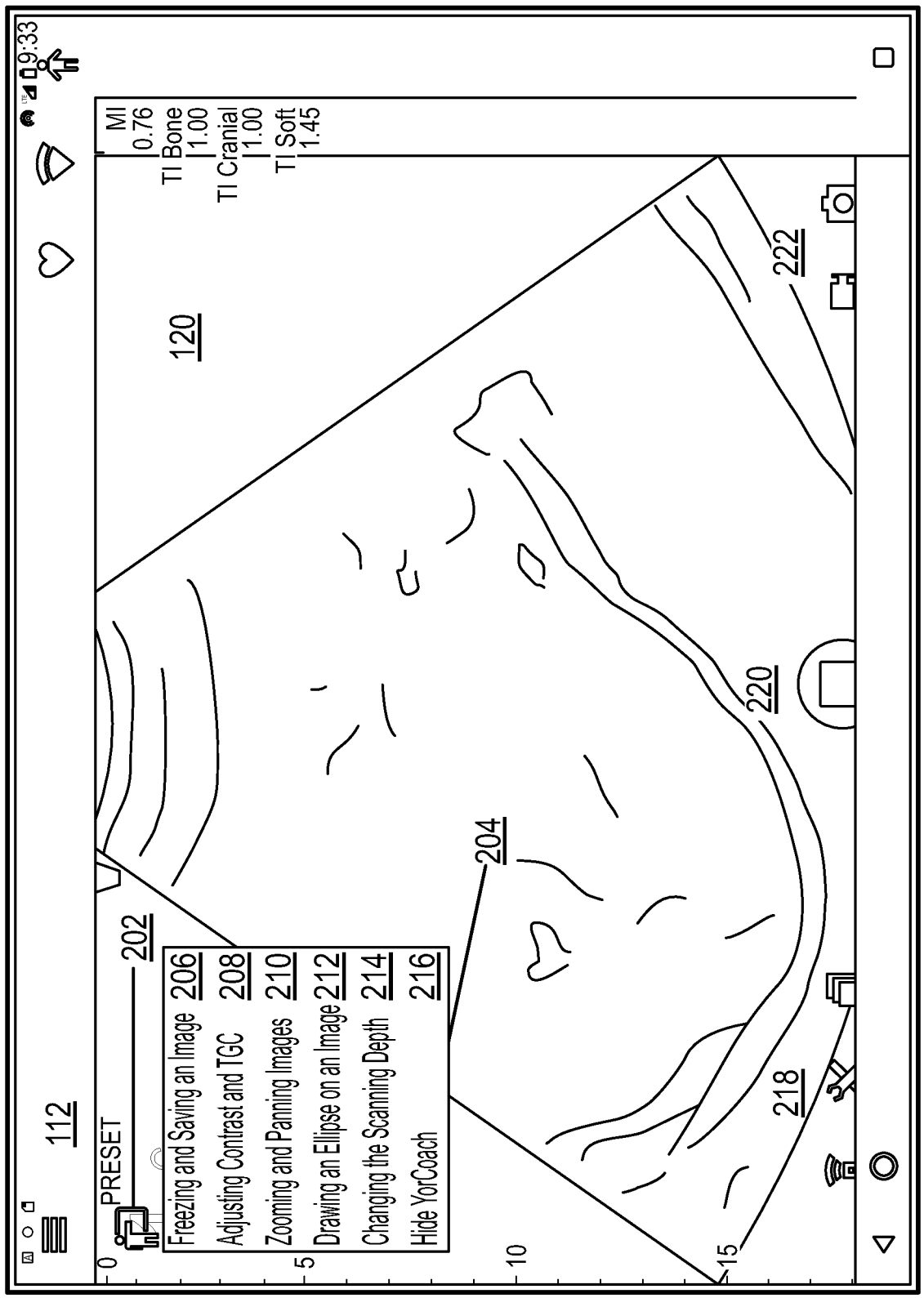
FIG. 2 is a picture of an example of a user interface that is generated and presented on a display, the user interface configured to have a control icon that is used to implement a user assistance program.

FIG. 2 illustrates an example display of a computer application being implemented by a processing system 102 on the interface 112 of FIG. 1. In some embodiments, FIG. 2 may correspond to a snapshot of a computer application that is generated and presented on a display. The processing system 102 is configured to generate and present information on the interface 112, and such operations of the processing system 102 and the interface 112 may be described herein as information being displayed or presented on the interface 112, or a panel of the interface 112, or that the interface 112 includes the described or illustrated feature. The interface 112 can include one or more portions, or panels (both which may be referred to as "panels" herein for ease of reference). Each of the one or more panels can present information to a user. each of the one or more panels of the interface 112 can be configured to receive a user input, for example, by the selection of a symbol or field displayed on the interface 112. In the example of FIG. 2, the computer application is an ultrasound imaging computer application. It will be understood that the computer application may be any type of computer application. In the example shown in FIG. 2, the interface 112 is displaying an ultrasound image being generated by an ultrasound imaging computer application. The ultrasound imaging computer application can be in communication with an ultrasound probe, or with stored information generated by the ultrasound probe. A proximal portion of the ultrasound image is displayed on an upper portion of the interface 112 and a distal portion of the ultrasound image is displayed on a lower portion of the interface 112 (the "upper" and "lower" portions relative to the orientation of the FIG. 2). The proximal portion is a portion of the ultrasound image that was closer to the ultrasound probe when the ultrasound image was captured, and thus corresponds to information in the object being imaged (e.g., a human or animal body) that was closer to the ultrasound probe and at a shallower "depth" in the object. The distal portion of the ultrasound image is a portion of the ultrasound image that was farther from the ultrasound probe when the image was captured, and thus corresponds to information in the object being imaged that was farther from the ultrasound probe and at a deeper "depth" in the object.

Various embodiments of the interface 112 can have at least one control icon 202. For ease or reference, the at least one control icon 202 may be referred to singularly even if referring to a plurality of control icons 202 displayed on different panels or at different times during processing. The control icon 202 may correspond to an icon being generated and displayed on the panel 120 of interface 112. The control icon 202 may be generated by a computer application, e.g., a training application. The control icon 202 may correspond to a symbol, a number, a word, etc. The control icon 202 may further include indicia indicating that the control icon 202 is a control icon (e.g., the control icon may include a title and/or depict a certain shape). Further, the control icon 202 may correspond to a training menu 204. In some embodiments, the control icon 202 may be a training menu 204. In other embodiments, the control icon 202 may cause the generation and display of a training menu 204 on the interface 112 based on an interaction by a user, for example, a click of the mouse on the control icon 202. Therefore, the at least one control icon 202 may include one or a plurality of icons presented on one or more panels of the interface 112 by a processing system in order to implement built-in user assistance capabilities.

The interface 112 may further generate and display various icons. Each icon can correspond to a particular operation. A set of icons 218 that correspond to operations performed when performing a process and/or using the system may also be generated and presented on the interface 112. For example, the icons 218 may correspond to copying an image, transmitting an image, printing an image, or other operations. The interface 112 can include a record button 220. The record button 220 may be used to capture a snapshot of an image at a given point in time. The interface 112 may further include a camera/video camera button 222. The camera/video camera button 222 may be used to switch between recording and taking a picture. It will be understood that in other implementations, the interface 112 may include more or less icons that correspond to more or less operations.

In order to generate a training menu 204, a user may interact with the control icon 202. The training menu 204 may be generated by the processing system and may provide certain training tasks for selection by a user. In the example of FIG. 2, the training tasks include: freezing and saving an image 206, adjusting contrast and TGC 208, zooming and panning images 210, drawing an ellipse on an image 212, and changing the scanning depth 214. In some embodiments, more or less training tasks may be presented by the training menu 204. Further, the training menu 204 may provide a subset of the training tasks that can be implemented for a given computer application. The training tasks that can be implemented for a given computer application may be based on the specific computer application. For example, the training tasks may be obtained from the training data based on the specific computer application. Further, the training tasks may include one or more general training tasks that are not specific to a particular computer application. The training menu 204 may further include a task (or functionality) to hide the training menu. In the example of FIG. 2, the training menu 204 includes Hide YorCoach 216 which can illustratively be used to hide the training menu 204. The training menu 204 may include additional tasks such as tasks to disable a training mode, enable training mode, exit a training task that is currently being run, etc. Upon disabling the training mode, the control icon 202 may be removed from the panel 120. Therefore, the training menu 204 may also include information about the specific training tasks that can be implemented by the processing system. The training menu 204 may further include training tasks ordered by certain factors such as popularity, most frequently used, shortest, longest, most complex, least complex, etc. Therefore, the training menu 204 may include a number of different training tasks and other tasks to be performed with respect to the computer application.

Each screen generated by the computer application for the interface 112 may include a different or unique control icon 202. In embodiments where multiple panels of the interface 112 are generated and presented, each panel may show a control icon 202. Further, as a user navigates between pages, images, or representations generated by a computer application, the control icon(s) 202 may be changed/updated. Further, the training menu 204 and the corresponding training tasks may be changed/updated such that certain training tasks are offered for certain pages, images, or representations, and not for others. Therefore, the control icon 202, the training menu 204, and the training tasks may be context sensitive in that they are based on the specific representation by the computer application.

Figure 3:
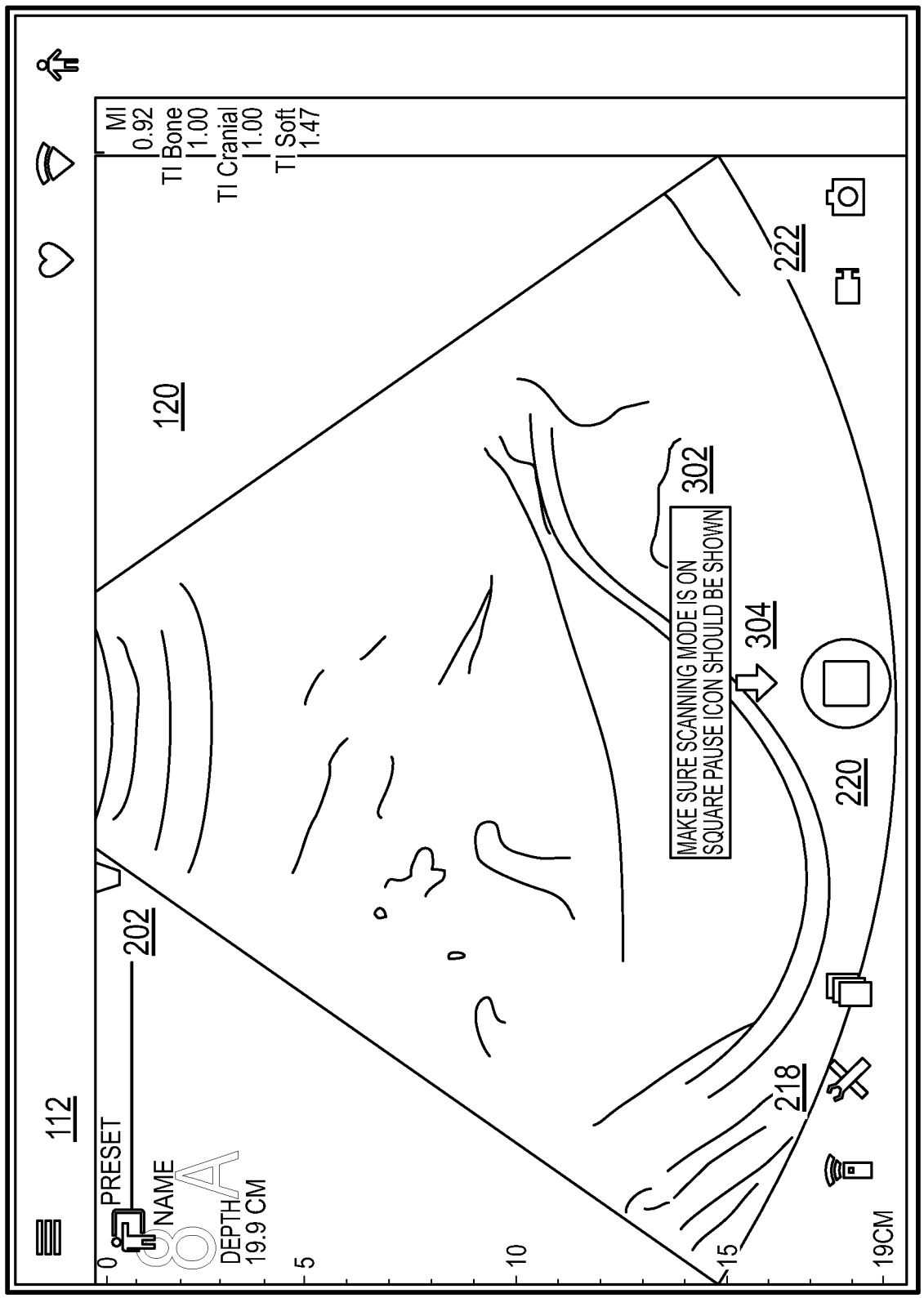
FIG. 3 is a picture of an example of the user interface illustrated in FIG. 2, now showing the image to include a training icon that is generated and presented on the bottom-half of the user interface. In this example, the training icon comprises a text box with instructions and an arrow illustrating a desired action.

FIG. 3 is a picture of another example of the interface 112 illustrated in FIG. 2, showing the control icon 202 and an implementation of a specific training task based on the ultrasound imaging computer application. In the example of FIG. 3, the training task being implemented is to train a user to adjust contrast and/or time gain compensation. The specific training task may be selected by a user through an interaction with the control icon 202 and/or a corresponding training menu. The training task may correspond to a series of actions or steps that must be performed in order to perform the corresponding operation. For example, a giving training task may be to capture a screenshot. In order to train the user to perform the training task, the training capabilities may walk the user through each action or step. In the example of a training task to capture a screenshot, a first action may be to open a screenshot tool, a second action may be to click on an icon in the screenshot tool, a third action may be to draw a box around the desired screenshot, and a fourth action may be to save the screenshot. The one or more actions may correspond to any level of granularity. In some embodiments, the user may specify the desired level of granularity. Each of the actions may correspond to a particular written description and one or more training icons that may be presented on the interface 112. Therefore, the user may interact with the control icon 202 in order to learn how to perform a certain task and the built-in training capabilities may provide instructions to the user (visually, audibly, etc.).

In FIG. 3, the training task being implemented by the computer application and/or the training application causes a written description 302 to be presented on the panel 120. The written description 302 may provide written instructions for the user in order to perform a first action associated with the training task. In the example of FIG. 3, the written description 302 is to make sure scanning mode is on square pause icon should be shown. The written description 302 may further include instructions to perform certain actions (e.g., press a certain button). The training task may further cause a training icon 304 to be generated on the panel 120. The training icon 304 may direct the user to a specific module, control, section, etc. of the panel 120. In the example of FIG. 3, the training icon 304 directs the user to the scanning or recording button 220. The training icon 304 may further represent a requested action such as a keyboard icon or series of keyboard icons (e.g., ctrl+f) or a user action (e.g., swiping on the screen). The training icon 304 may correspond to the written description 302 such that the written description 302 describes an element or action that should be seen, performed, etc. at the location designated by the training icon 304. The training task being implemented may further cause a training title to be presented on the panel 120 (not shown in FIG. 3). For example, the panel 120 may include a box with the training title "performing a scan." One or more of the training title, the training icon 304, the written description 302, the control icon 202 may be colored in a different color, bolded, enlarged, underlined, or otherwise modified so as to alert the user that these may be used for training. Therefore, the training task may include a first action with a written description 302 and/or a training icon 304.

The training application and/or the computer application may detect when the first action has been completed and may present a second action. In some embodiments, the user may interact (e.g., click or tap the training icon or the control icon) with the panel 120 to indicate that the first action has been completed. Further, a second training icon may be implemented on the panel 120 to allow the user to return to a previously completed action. For example, the second training icon may be a backward arrow. In some embodiments, the computer application and/or the training application may detect that the first action has not been completed and may not allow the user to move on to the second action of the training task. In other embodiments, the computer application and/or the training application may detect that the first action has not been completed and may prompt the user to complete or skip the first action. Each training task may correspond to a tree of steps where each branch of the tree corresponds to certain user responses to previous steps. The user may progress through a series of actions corresponding to the training task. Upon completing the final action or step of the training task, the computer application and/or the training application may indicate that the training is complete. For example, the training icon 304 may be moved to the control icon 202 or the training menu or a completion message may be displayed on the panel 120. Therefore, the user may complete a training process.

Figure 4:
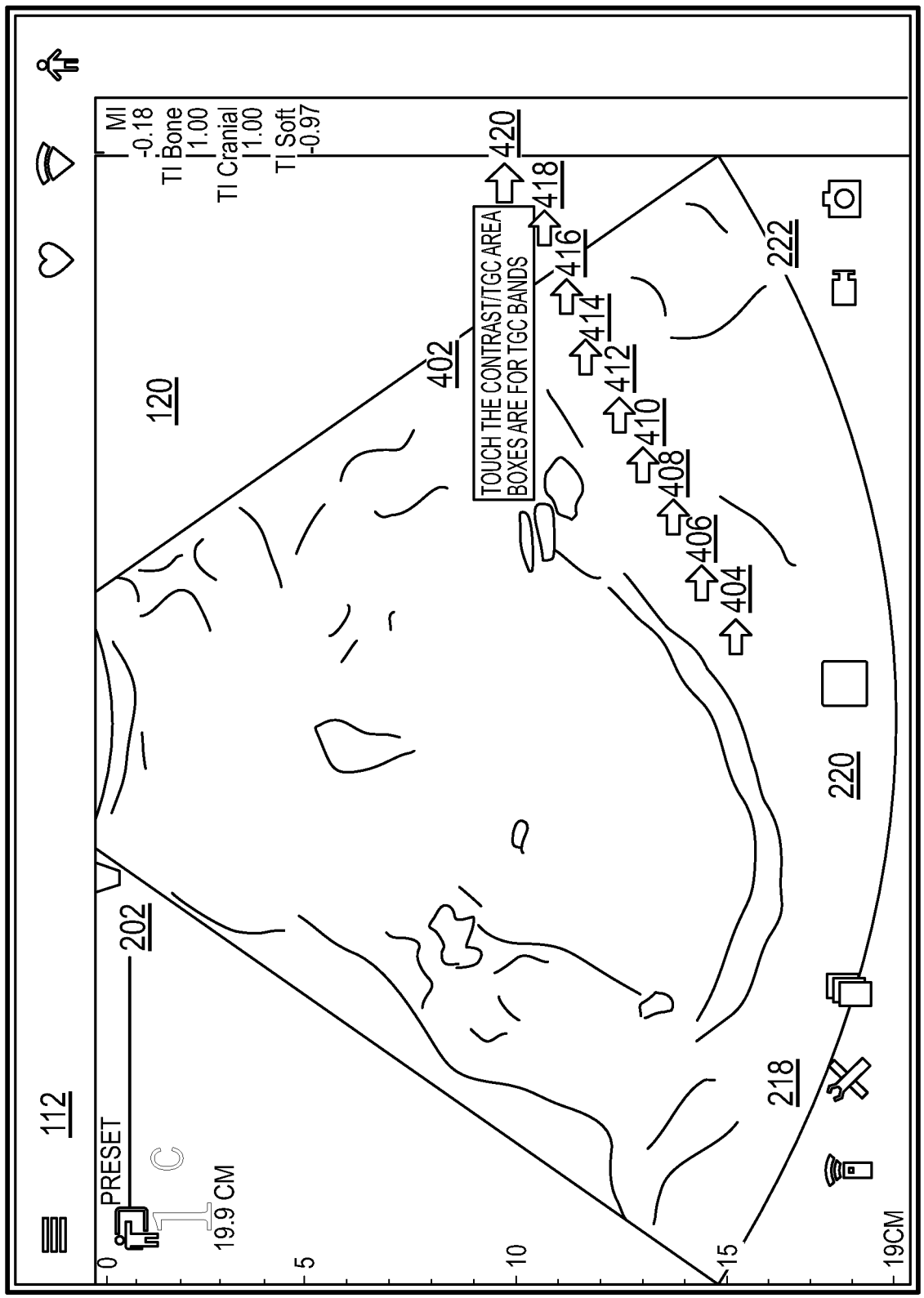
FIG. 4 is a further picture of an example of the user interface illustrated in FIG. 2, now showing the image to include a series of training icons. In this example, the series of training icons represent a series of desired actions. Further, the series of training icons comprise a text box with instructions.

FIG. 4 is a picture of another example of the interface 112 illustrated in FIG. 2, showing the control icon 202 and an implementation of a specific training task based on the ultrasound imaging computer application. FIG. 4 may correspond to the training task of FIG. 3, training a user to scan an ultrasound image. Whereas FIG. 3 corresponded to a first action or step of the training task, FIG. 4 may correspond to a second action or step of the training task. The image in the panel 120 may be presented based upon a completion of a previous action (e.g., the first action of FIG. 3). In some embodiments, the image in the panel 120 may be presented based upon a user interaction (e.g., a click of a skip button). Therefore, the user may interact with the interface 112 in order to move to a second action of the training task.

In FIG. 4, the second action of the training task may cause a second written description 402 to be presented on the panel. The second written description 402 may correspond to the second action and may illustrate a second desired action to be taken by the user. In the example of FIG. 4, the second written description 402 is to touch the contrast/TGC area boxes are for TGC bands. The second action may further cause one or more training icons to be presented on the panel 120. The one or more training icons may correspond to a series of training icons. The series of training icons may correspond to multiple steps such that the movement between steps of the training icons is animated. For example, a first training icon may be located at or near the location of the first action and a series of training icons may lead the user to the location of the second action. In the example of FIG. 4, the series of training icons 404, 406, 408, 410, 412, 414, 416, 418, and 420 guide the user from the location of the first action to the location of the second action. Therefore, the training task may aid the user in performing the second action of the training task and any further actions of the training task.

Figure 5:
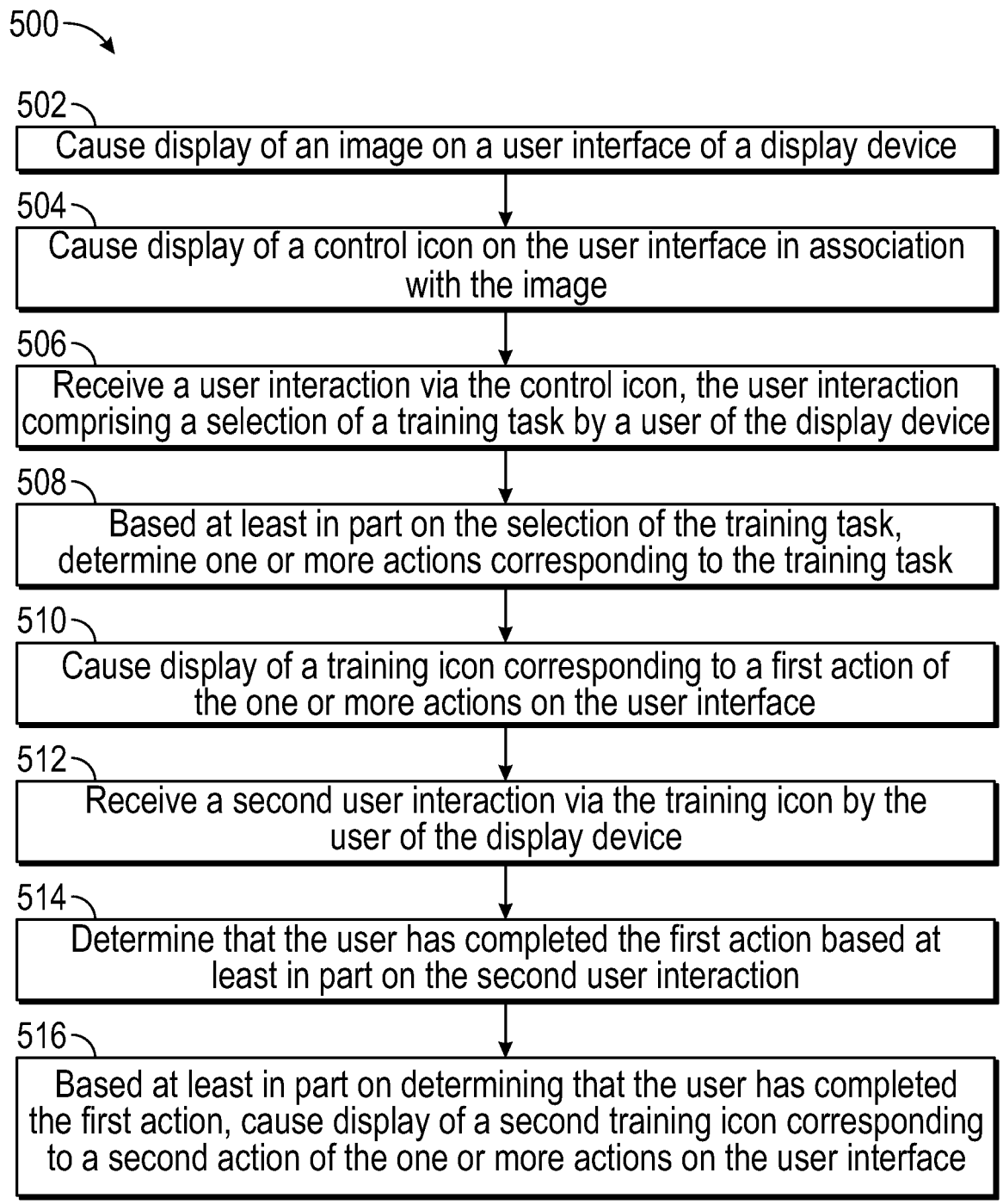
FIG. 5 is a flowchart illustrating a method for implementing a user assistance (or training) program.

FIG. 5 is a flowchart illustrating a method 500 for providing a training capability for a computer application. The method can be performed, for example, on the processing system 102 illustrated in FIG. 1. In some embodiments, the processing system 102 may be an ultrasound imaging processing system 102 that receives ultrasound images and the computer application may be run on the processing system to perform certain operations. At block 502, the method 500 begins, causing display of an image on a user interface of a display device. In some embodiments, the image may be an ultrasound image. The image may be displayed with certain characteristics or values. For example, the image may be displayed at a default zoom level, a default pan, etc. At block 504 the method 500 continues, causing display of a control icon on the user interface in association with the image. The control icon may be overlaid on the image. In some embodiments, the control icon may be displayed separately from the image (e.g., the control icon may be displayed on a separate panel). In other embodiments, the control icon can be displayed adjacent to the image. The control icon may correspond to a predetermined size, shape, color, etc. The control icon may be enlarged, bolded, colored. Further, the control icon may be disabled based on an interaction with the control icon and subsequently enabled based on an interaction with the panel.

At block 506, the method can continue receiving a user interaction with the control icon. The user interaction may be received via an input device or any other interaction with the display device. The user interaction may comprise a selection of a training task by a user of the display device. In some embodiments, a first user interaction may cause a menu of training tasks to be presented and a second user interaction may select a specific training task. An example of the menu is illustrated in FIG. 3. At block 508, the method can continue determining actions corresponding to the training task. The display device may determine one or more actions associated with the training task based upon the selection of the training task. The display device may query a training data store to determine the actions associated with the training task.

At block 510, the method can continue causing display of a training icon corresponding to a first action of the one or more actions. The training icon may be displayed on the user interface. In some embodiments, a written description may also be displayed. In other embodiments, a written description may be displayed instead of the training icon. The training icon may correspond to a desired action to be performed by the user in order to effectuate the first action. At block 512, the method can continue receiving a second user interaction by the user of the display device. The second user interaction can comprise an interaction with one or more of the control icon, the training icon, the panel, the written description, etc.

At bock 514, the method can continue determining that the user has completed the first action based at least in part on the second user interaction. The display device may determine that the second user interaction is associated with the first action and indicates that the first action has been completed. In some embodiments, the display device may determine that the second user interaction indicates that the user desires to skip the first action. At block 516, the method can continue causing display of a second training icon on the user interface. The second training icon can correspond to a second action of the one or more actions associated with the training task. The second training icon may be displayed based at least in part on determining that the first action has been completed. Various examples of such methods can include any of the functionality and/or operations described herein.

Figure 6:
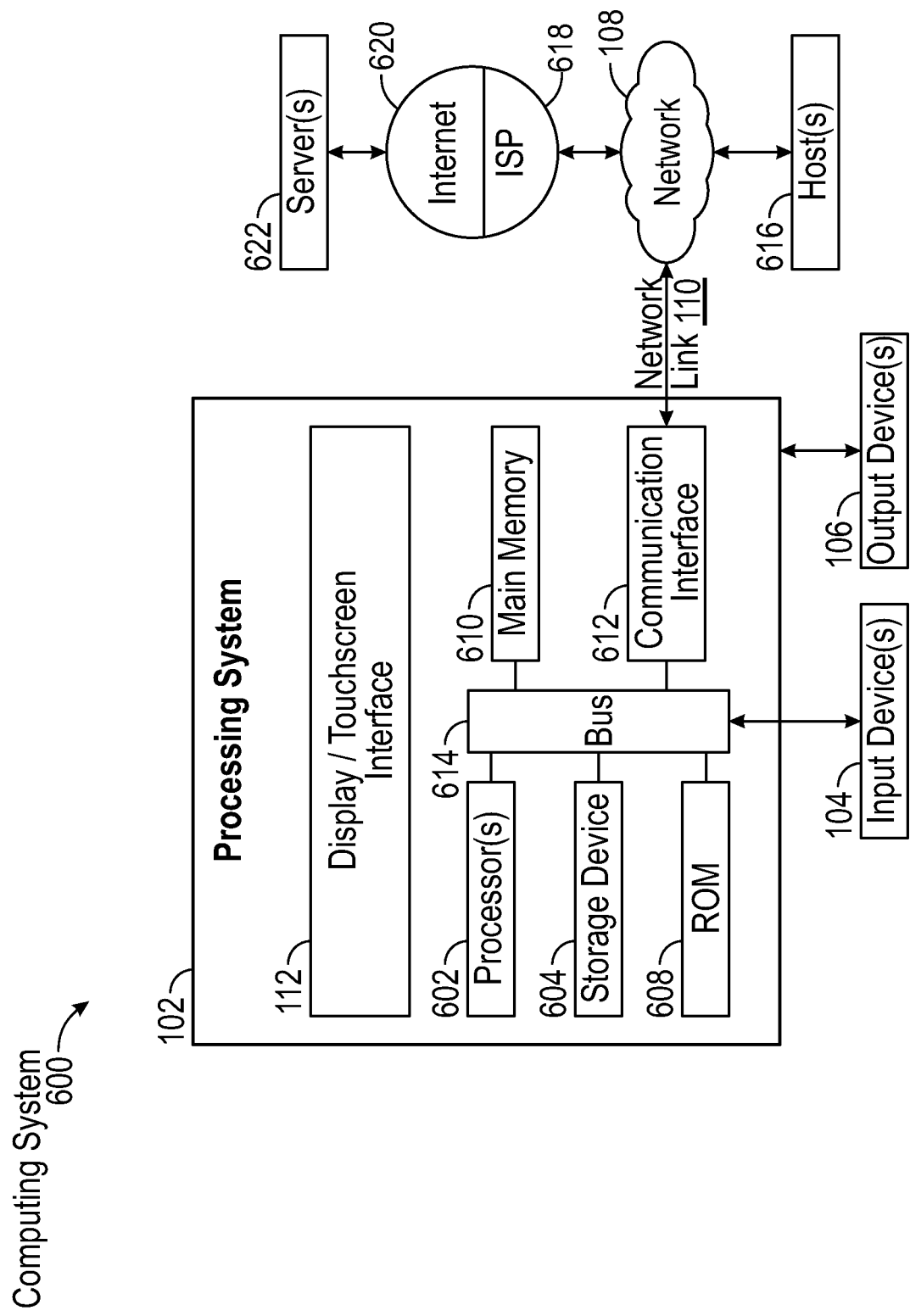
FIG. 6 is a block diagram illustrating an example of a computing system that is adapted to perform functionality described herein.

FIG. 6 is a block diagram illustrating an example of a computing system 600 that is adapted to perform functionality described herein relating to causing presentation of an image on a user interface of a interface 112 along with a training icon that provides a built-in training capability in order to train users in performing various operations on a computer application being run by the processing system 102. As illustrated in FIG. 6, the computing system includes input device(s) 104 (e.g., an ultrasound probe) in communication with the processing system (computer system) 102. The input device(s) 104 can be connected to the processing system 102 via a wired or a wireless connection that allows the input device(s) 104 to provide data to the processing system 102 and receive control signals or instructions from the processing system. The computing system 600 may further include one or more output device(s) that are in communication with the processing system 102 in order to receive date output by the processing system 102.

In order to communicate with the input device(s) 104, the processing system 102 includes a bus 614 or other communication mechanism for communicating information, and a hardware processor (or multiple processors) 602 coupled with bus 614 for processing information. Hardware processor(s) 602 may be, for example, one or more general purpose microprocessors.

The processing system 102 also includes a main memory 610, such as a random access memory (RAM), cache and/or other dynamic storage devices, coupled to bus 614 for storing instructions to be executed by processor 602. Main memory 610 also may be used for storing temporary variables or other intermediate information during execution of instructions to be executed by processor 602. Such instructions, when stored in storage media accessible to processor 602, render the processing system 102 into a special-purpose machine that is customized to perform the operations specified in the instructions. The main memory 610 may, for example, include instructions to display a training icon for a computer application and may specify the training tasks that may be provided for a specific computer application. Further, the main memory may include instructions indicating the training tasks that can be implemented for each page associated with a computer application.

The processing system 102 further includes a read only memory (ROM) 608 or other static storage device coupled to bus 614 for storing static information and instructions for processor 602. A storage device 604, such as a SSD drive, magnetic disk, optical disk, or USB thumb drive (Flash drive), etc., is provided and coupled to bus 614 for storing information and instructions.

The processing system 102 may be coupled via bus 614 to a interface 112 (for example, a touch screen display) for displaying information to a computer user. One or more input device(s) 104 which may include alphanumeric and other keys and/or provide cursor control (e.g., mouse, trackball, or cursor direction keys) for communicating direction information and command selections to processor 602 and for controlling cursor movement on interface 112 can be coupled to bus 614 for communicating information and command selections to processor 602.

The processing system 102 may include a user interface module to implement a GUI that may be stored in a mass storage device as computer executable program instructions that are executed by the computing device(s). The processing system 102 may further, as described below, implement the techniques described herein using customized hard-wired logic, one or more ASICs or FPGAs, firmware and/or program logic which in combination with the computer system causes or programs the processing system 102 to be a special-purpose machine. According to one embodiment, the techniques herein are performed by The processing system 102 in response to processor(s) 602 executing one or more sequences of one or more computer readable program instructions contained in main memory 610. Such instructions may be read into main memory 610 from another storage medium, such as storage device 604. Execution of the sequences of instructions contained in main memory 610 causes processor(s) 602 to perform the process steps described herein. In alternative embodiments, hard-wired circuitry may be used in place of, or in combination with, software instructions.

Various forms of computer readable storage media may be involved in carrying one or more sequences of one or more computer readable program instructions to processor 602 for execution. For example, the instructions may initially be carried on a magnetic disk or solid state drive of a remote computer. The remote computer can load the instructions into its dynamic memory and send the instructions over a network link 110. Bus 614 carries the data to main memory 610, from which processor 602 retrieves and executes the instructions. The instructions received by main memory 610 may optionally be stored on storage device 604 either before or after execution by processor 602.

The processing system 102 also includes a communication interface 612 coupled to bus 614. Communication interface 612 provides a two-way data communication coupling to the network link 110 that is connected to the network 108. For example, communication interface 612 may be an integrated services digital network (ISDN) card, cable modem, satellite modem, or a modem to provide a data communication connection to a corresponding type of telephone line. As another example, communication interface 612 may be a local area network (LAN) card to provide a data communication connection to a compatible LAN (or WAN component to communicate with a WAN). Wireless links may also be implemented. In any such implementation, communication interface 612 sends and receives electrical, electromagnetic or optical signals that carry digital data streams representing various types of information.

Network link 110 typically provides data communication through one or more networks to other data devices. For example, network link 110 may provide a connection through the network 108 to host(s) 616 or to data equipment operated by an Internet Service Provider (ISP) 618. ISP 618 in turn provides data communication services through the world wide packet data communication network now commonly referred to as the "Internet" 620. The network 108 and the Internet 620 both use electrical, electromagnetic or optical signals that carry digital data streams. The signals through the various networks and the signals on network link 110 and through communication interface 612, which carry the digital data to and from the processing system 102, are example forms of transmission media. The processing system 102 can send messages and receive data, including program code, through the network(s), network link 110 and communication interface 612. In the Internet example, a server 622 might transmit a requested code for an application program through Internet 620, ISP 618, network 108, the network link 110, and communication interface 612. The received code may be executed by processor 602 as it is received, and/or stored in storage device 604, or other non-volatile storage for later execution.

Figure 7:
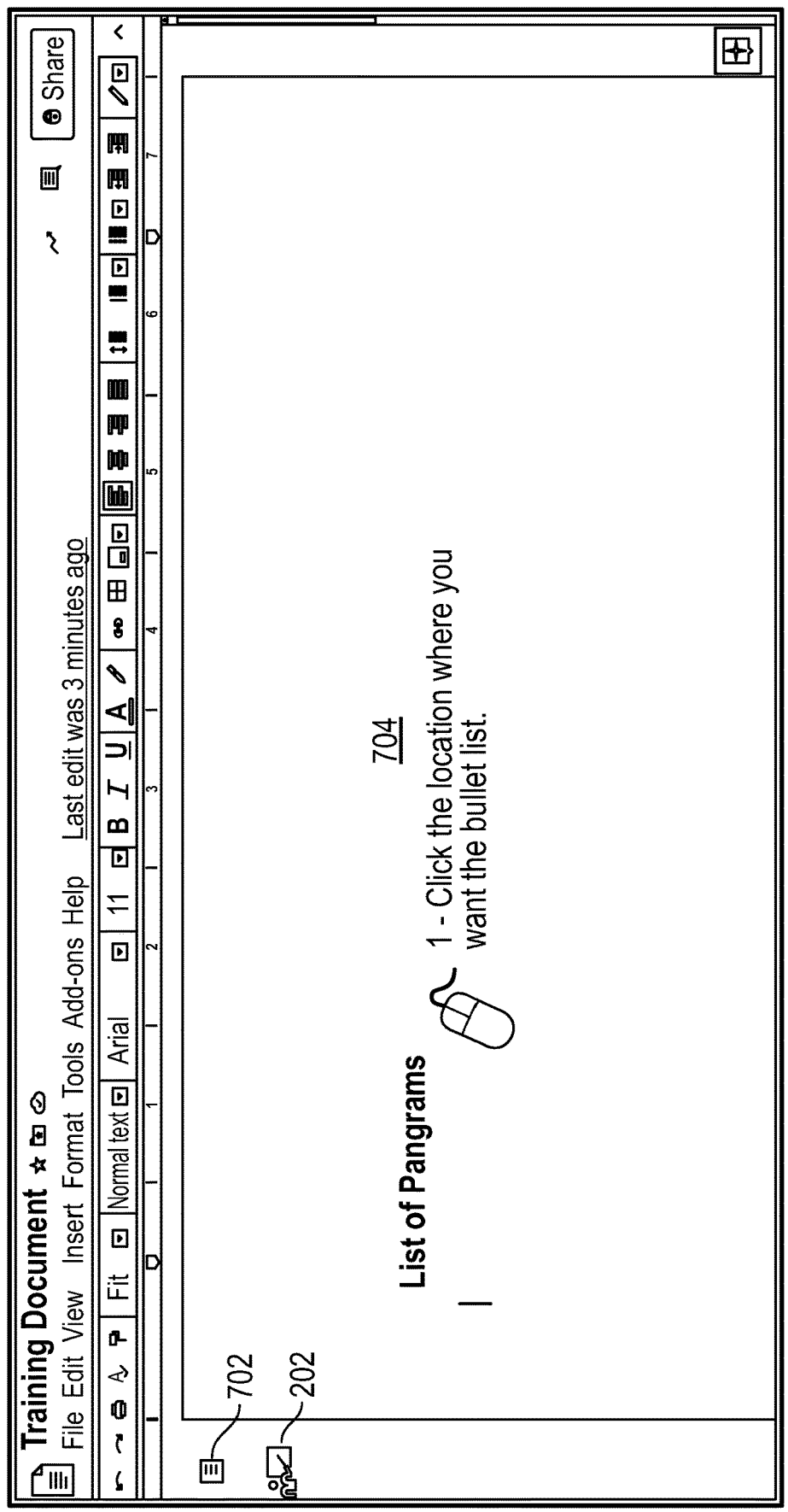
FIG. 7 is a further picture of an example user interface, now showing a control icon and a training icon.
Figure 8:
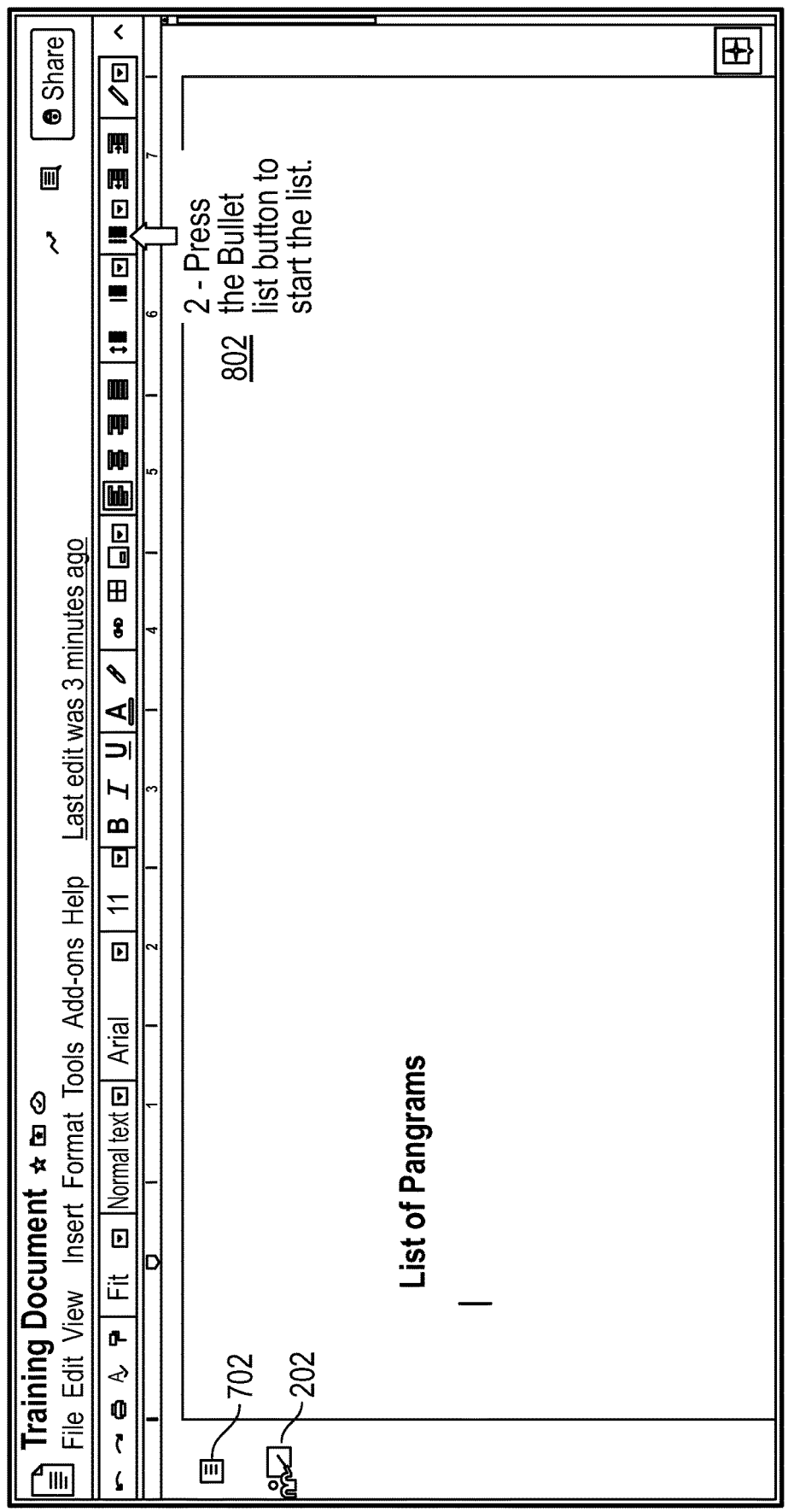
FIG. 8 is a further picture of an example user interface, now showing a control icon and a training icon.
Figure 9:
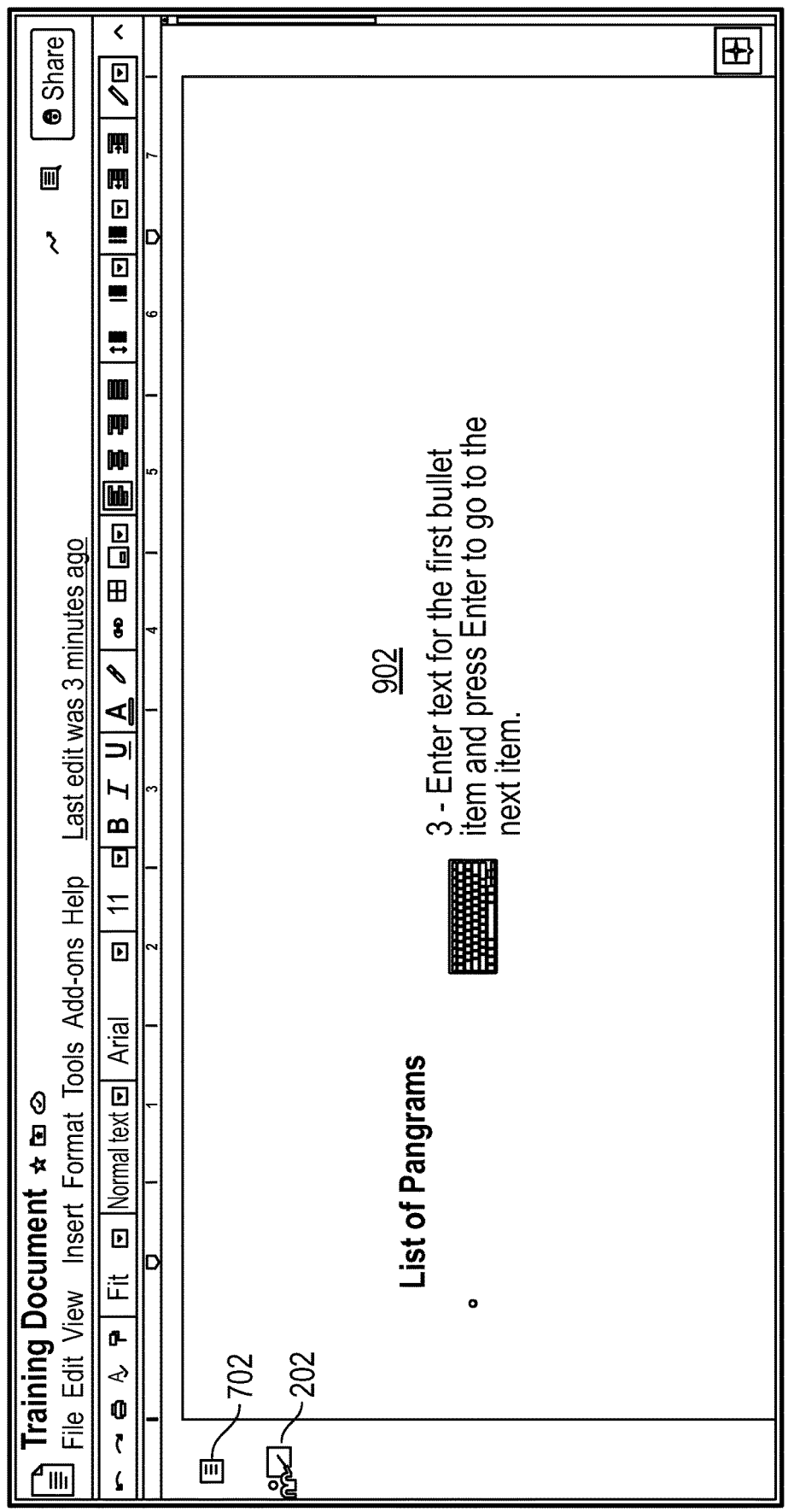
FIG. 9 is a further picture of an example user interface, now showing a control icon and a training icon.
Figure 10:
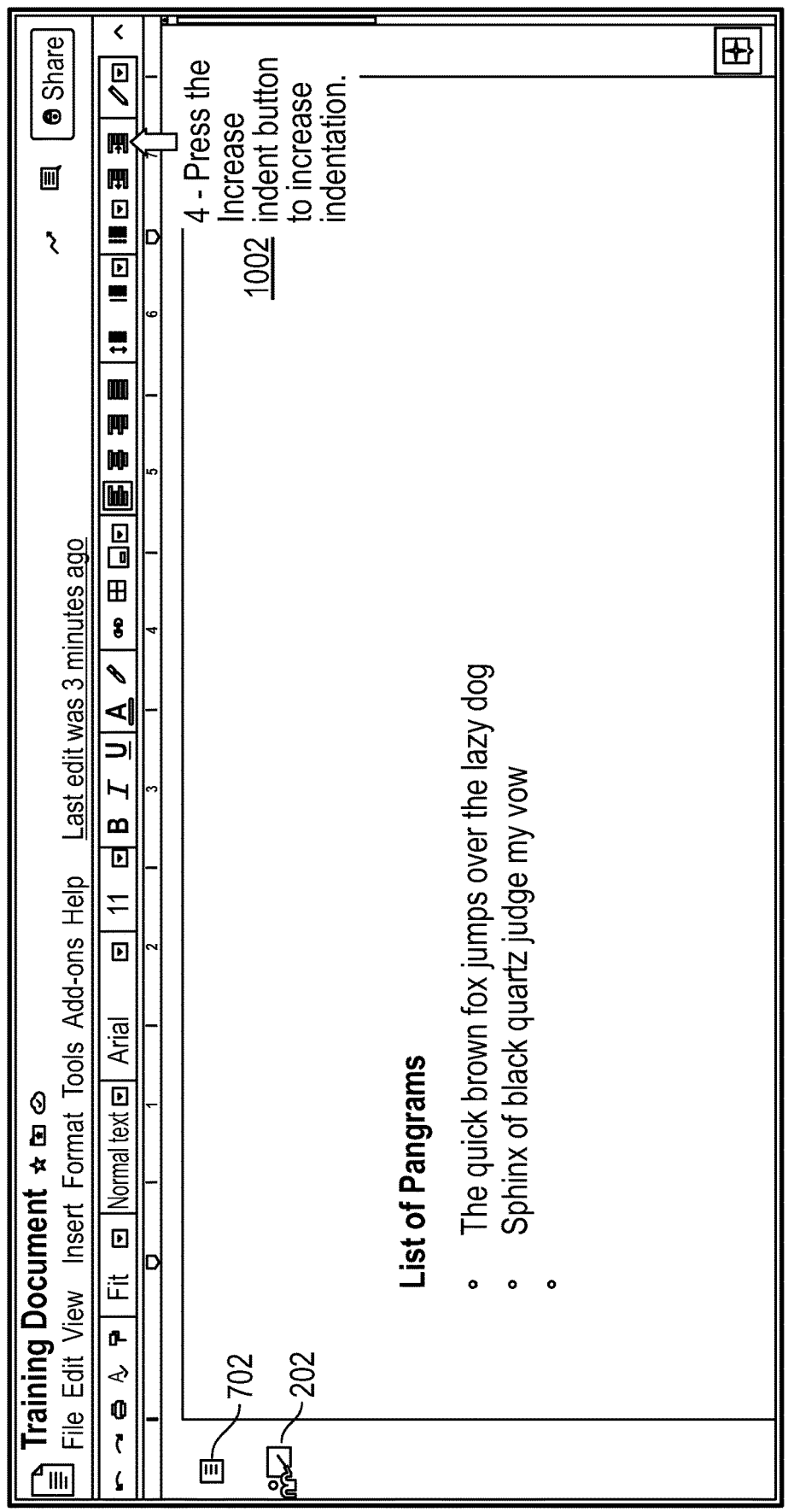
FIG. 10 is a further picture of an example user interface, now showing a control icon and a training icon.
Figure 11:
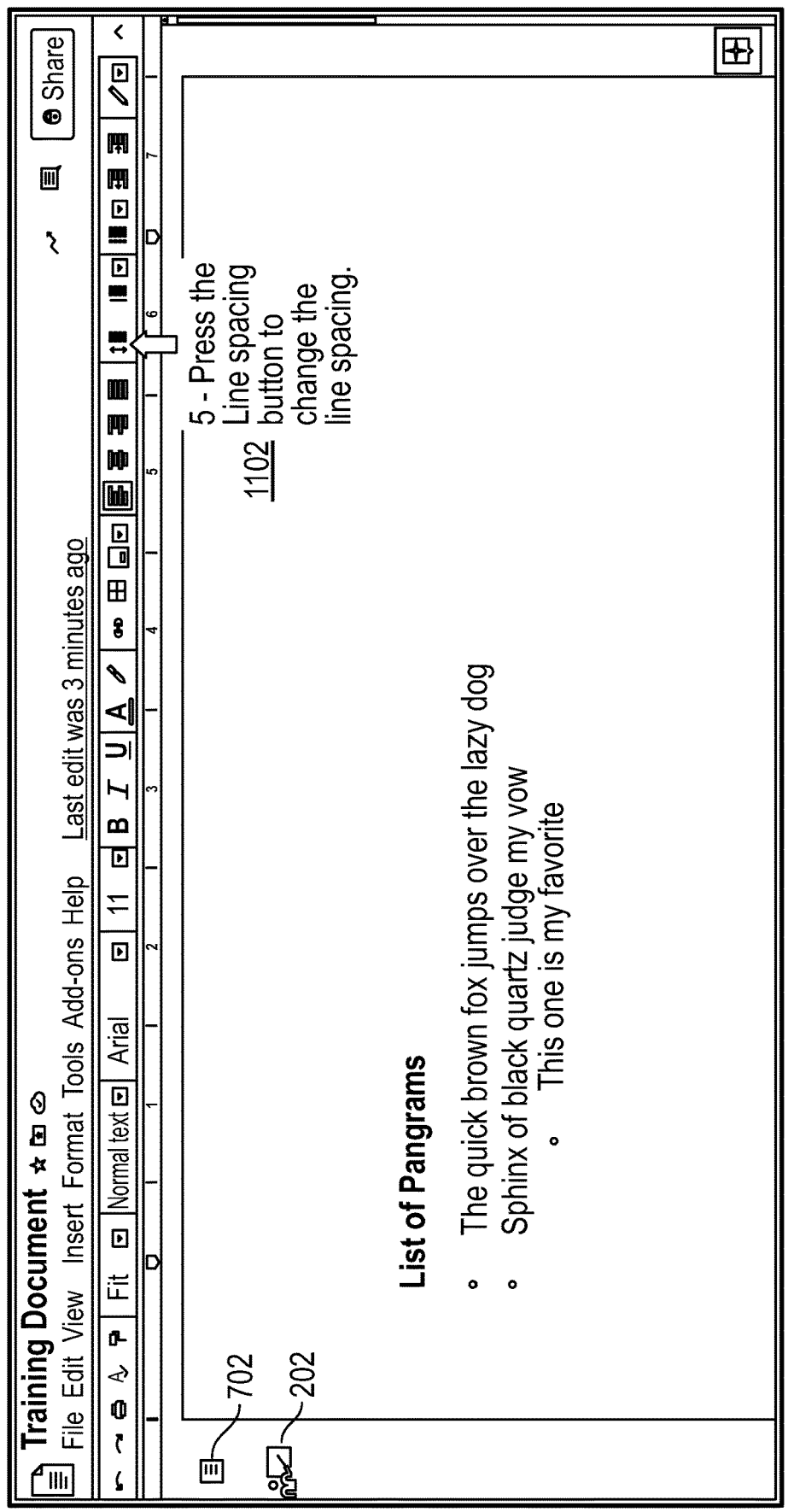
FIG. 11 is a further picture of an example user interface, now showing a control icon and a training icon.
Figure 12:
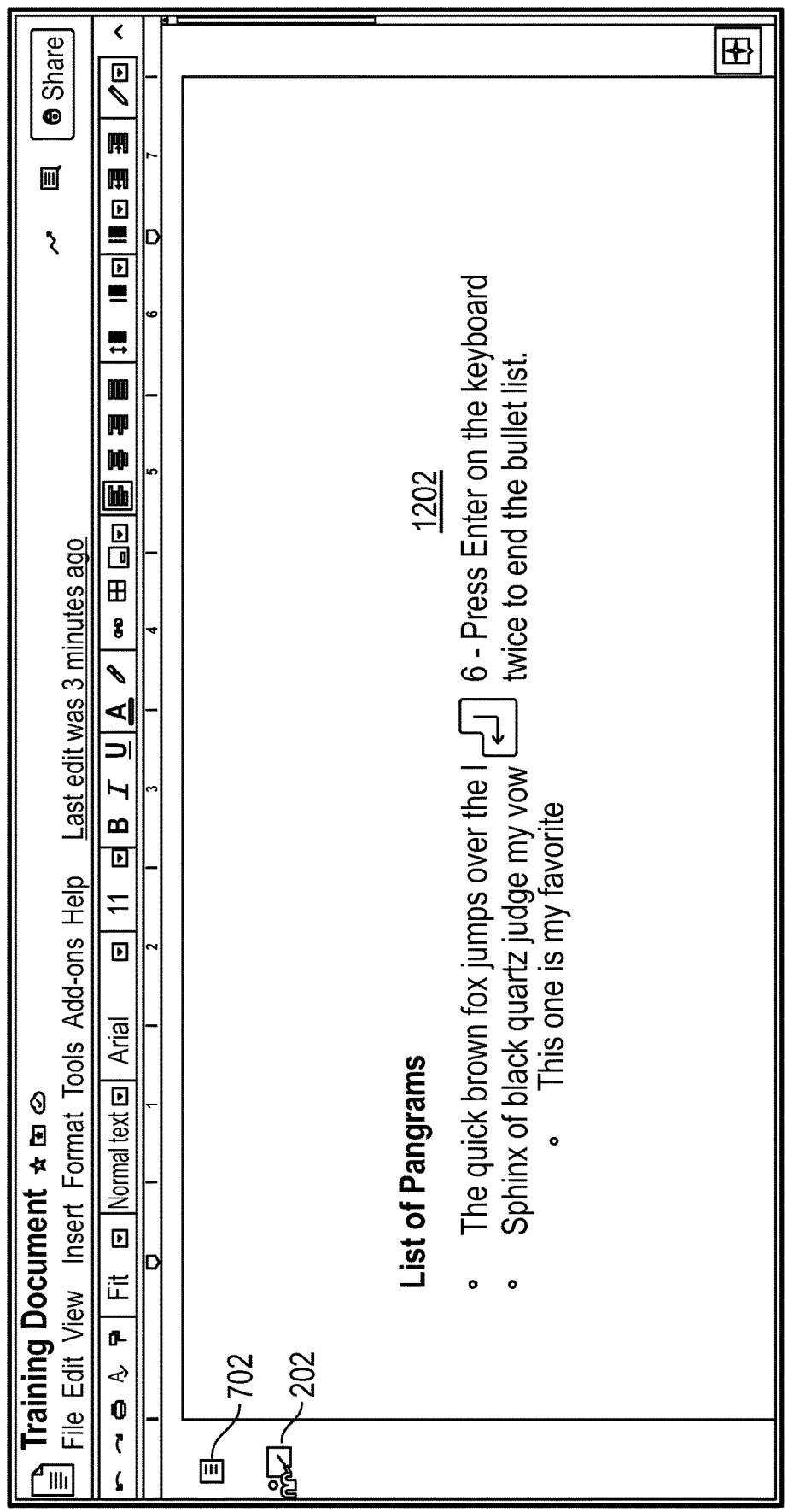
FIG. 12 is a further picture of an example user interface, now showing a control icon and a training icon.

FIG. 7, FIG. 8, FIG. 9, FIG. 10, FIG. 11, FIG. 12, FIG. 13, FIG. 14, FIG. 15, FIG. 16, FIG. 17, FIG. 18, and FIG. 19 are each a picture of another example of the interface 112 illustrated in FIG. 2, showing the control icon 202 and an implementation of a specific training task based on a computer application. FIG. 7, FIG. 8, FIG. 9, FIG. 10, FIG. 11, and FIG. 12 may correspond to a particular training task (e.g., training a user to create a bulleted list) and show the control icon 202 and a menu icon 702. In some embodiments, the menu icon 702 may provide access to the control icon 202. FIG. 7 may include a first training icon 704 corresponding to a first step of the training task. FIG. 8 may include a second training icon 802 corresponding to a second step of the training task. FIG. 9 may include a third training icon 902 corresponding to a third step of the training task. FIG. 10 may include a fourth training icon 1002 corresponding to a fourth step of the training task. FIG. 11 may include a fifth training icon 1102 corresponding to a fifth step of the training task. FIG. 12 may include a sixth training icon 1202 corresponding to a sixth step of the training task. It will be understood that the training task may include more, less, or different steps. In some embodiments, each training icon may be iteratively presented based on completion of a corresponding, prior step. In other embodiments, multiple training icons may be presented at the same time.

Figure 13:
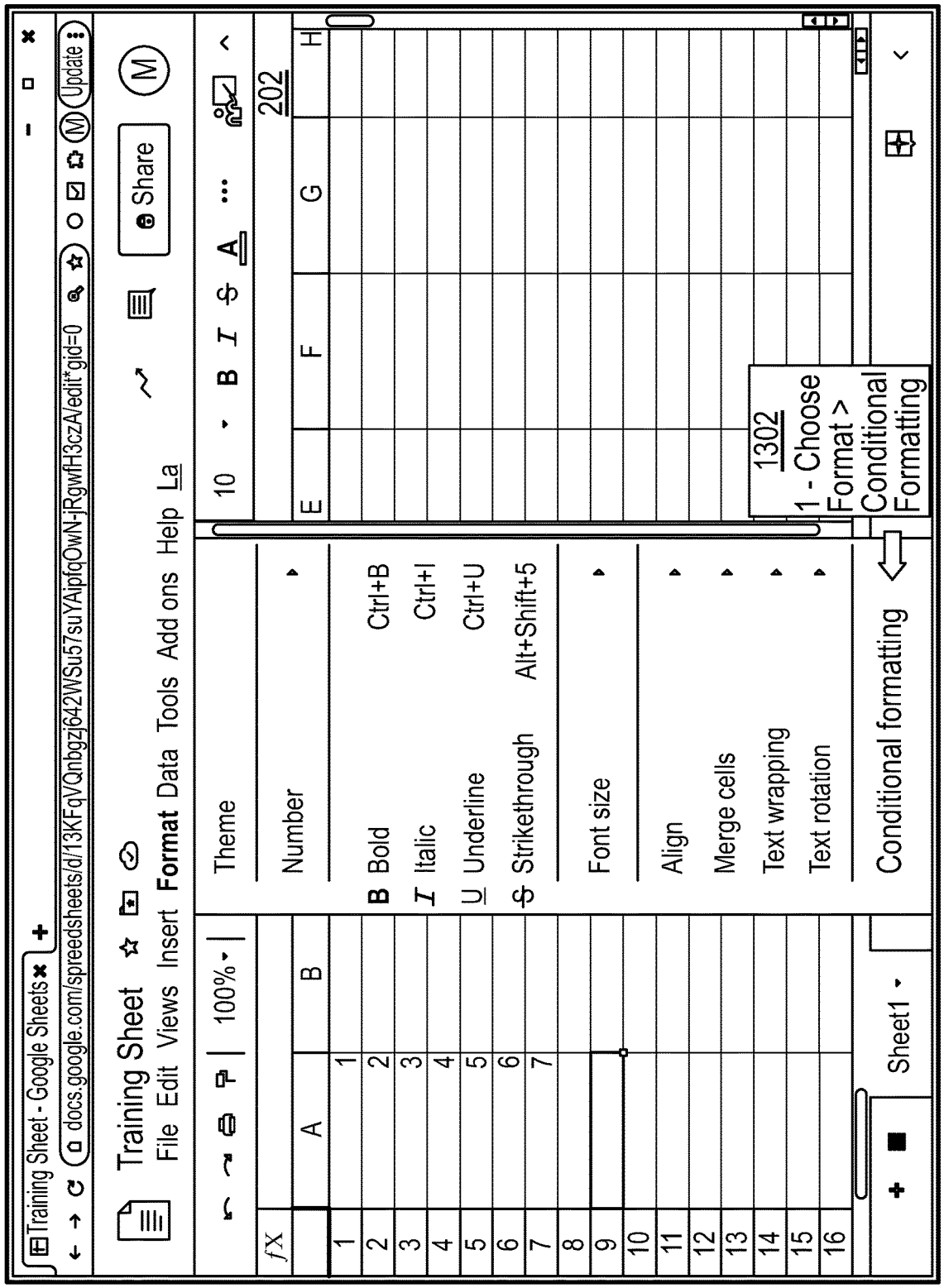
FIG. 13 is a further picture of an example user interface, now showing a control icon and a training icon.
Figure 14:
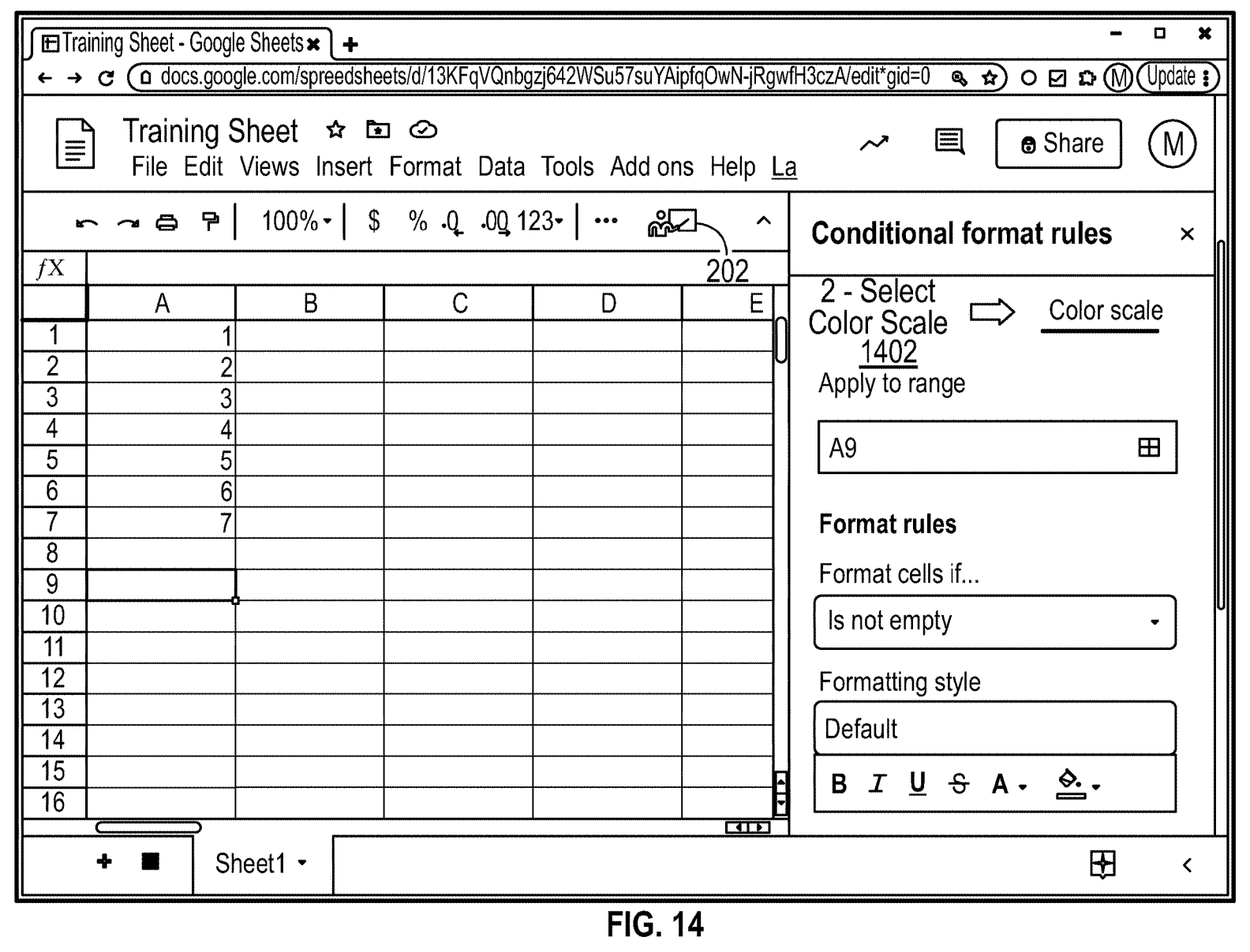
Figure 15:
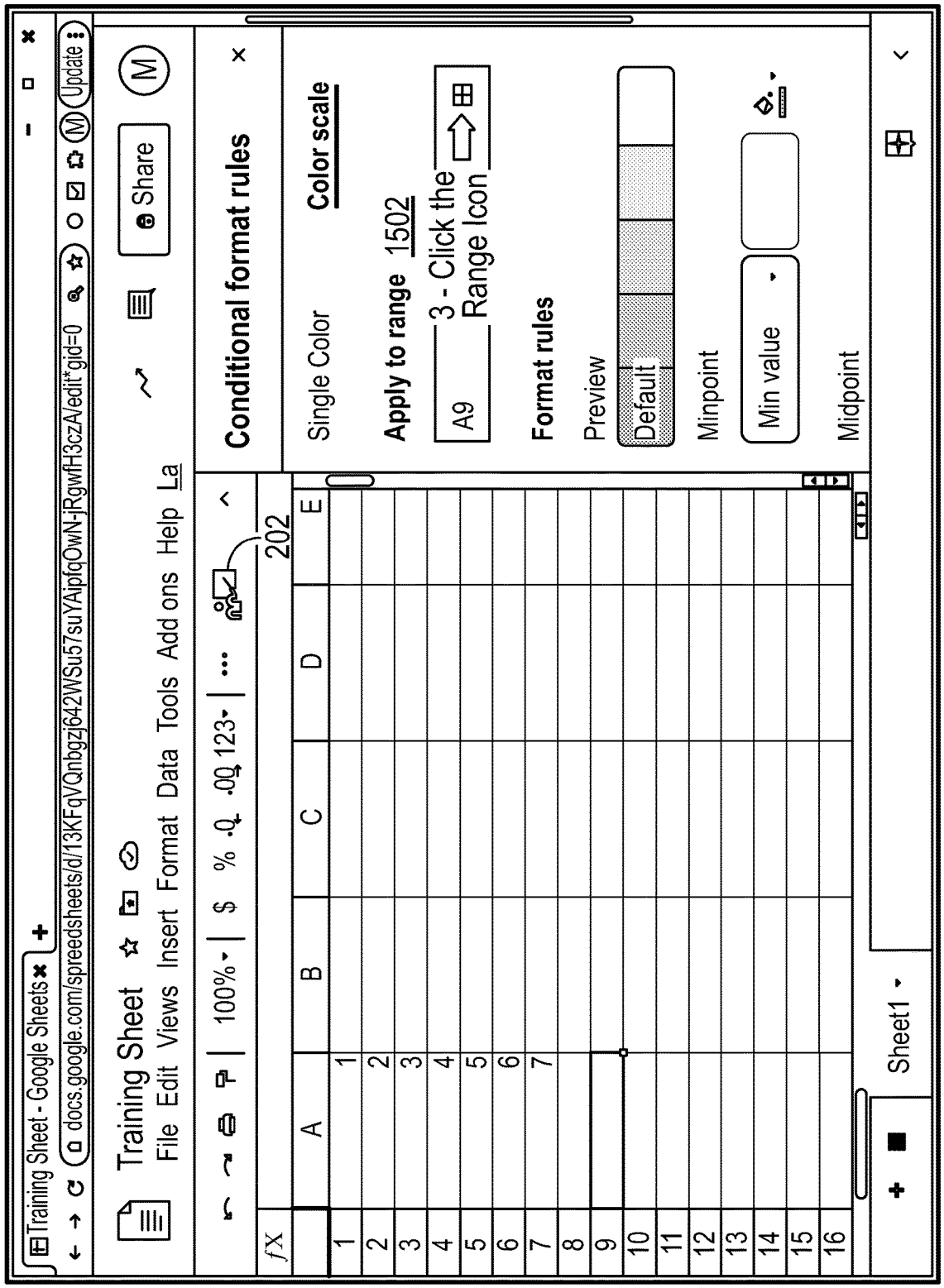
FIG. 15 is a further picture of an example user interface, now showing a control icon and a training icon.
Figure 16:
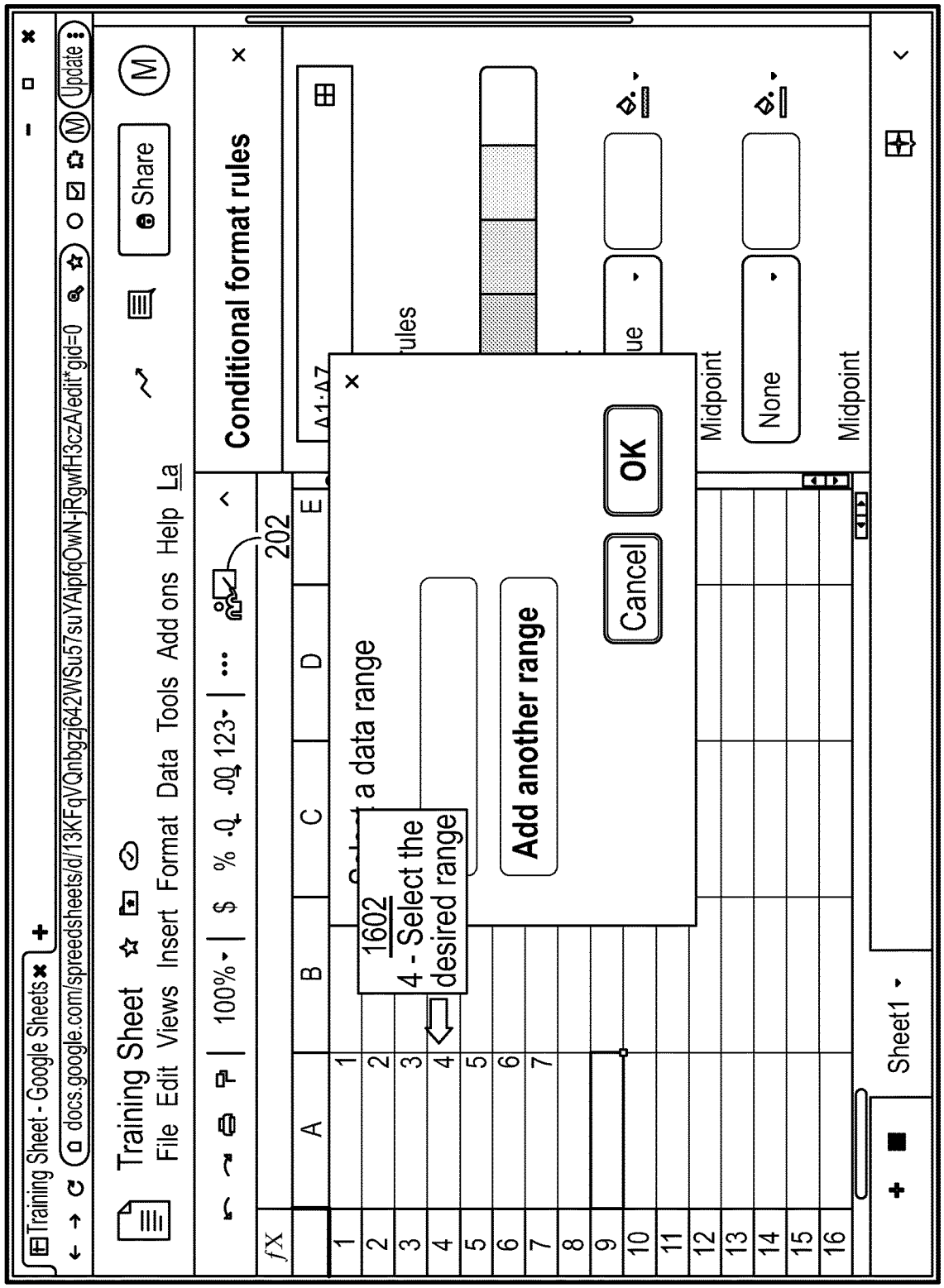
FIG. 16 is a further picture of an example user interface, now showing a control icon and a training icon.
Figure 17:
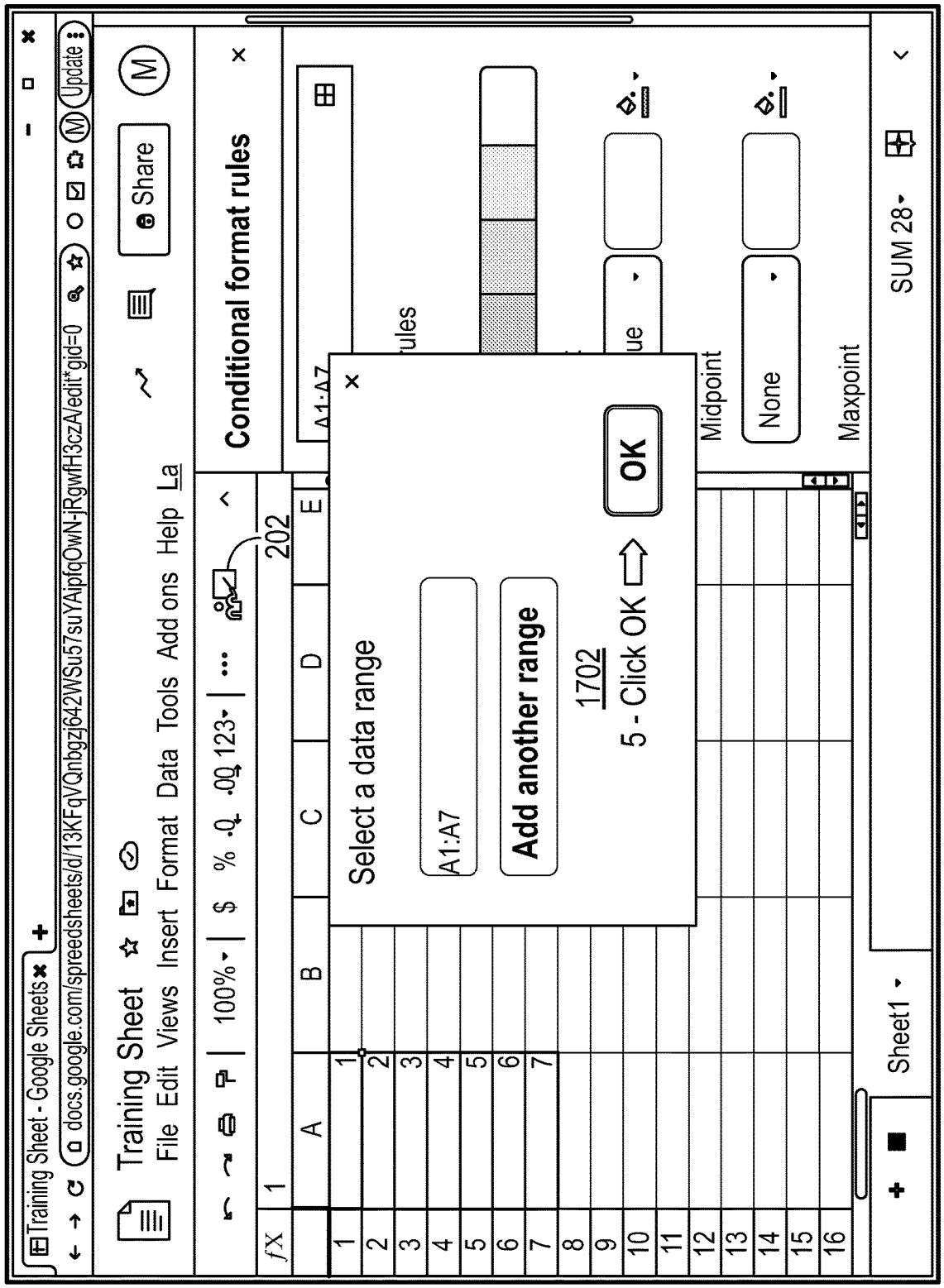
FIG. 17 is a further picture of an example user interface, now showing a control icon and a training icon.
Figure 18:
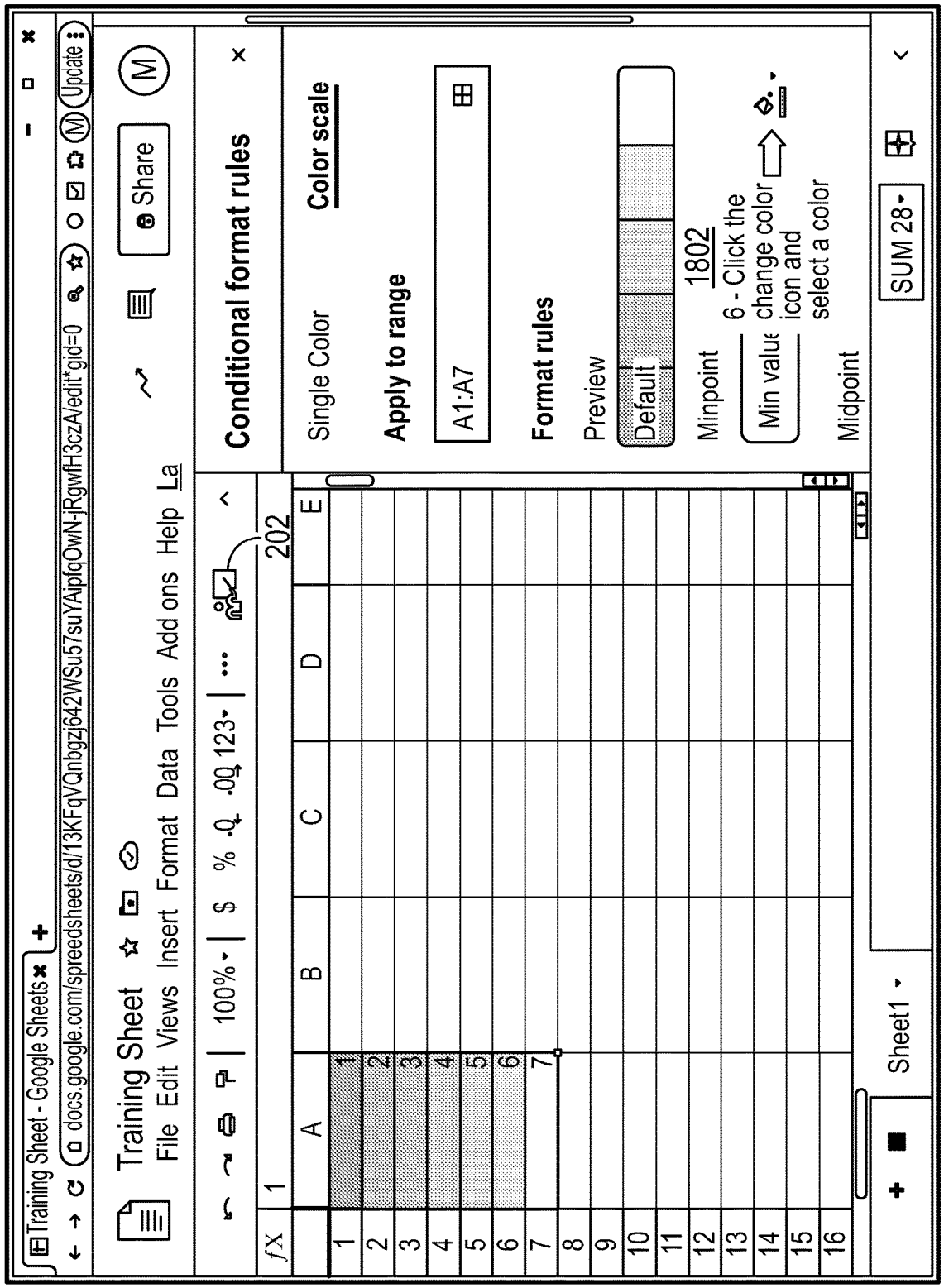
FIG. 18 is a further picture of an example user interface, now showing a control icon and a training icon.
Figure 19:
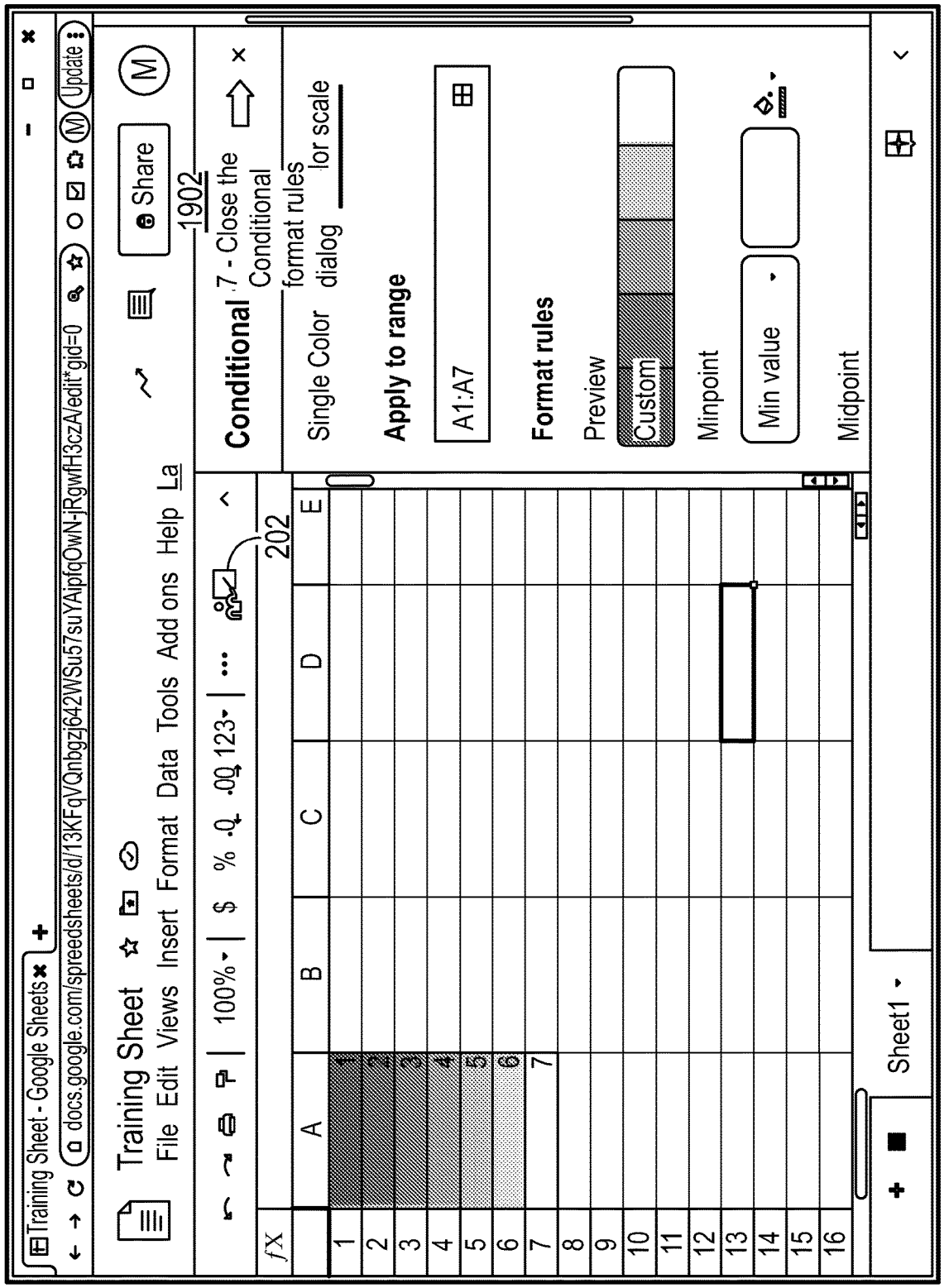
FIG. 19 is a further picture of an example user interface, now showing a control icon and a training icon.

FIG. 13, FIG. 14, FIG. 15, FIG. 16, FIG. 17, FIG. 18, and FIG. 19 may correspond to a particular training task (e.g., training a user to apply conditional formatting) and show the control icon 202. FIG. 13 may include a first training icon 1302 corresponding to a first step of the training task. FIG. 14 may include a second training icon 1402 corresponding to a second step of the training task. FIG. 15 may include a third training icon 1502 corresponding to a third step of the training task. FIG. 16 may include a fourth training icon 1602 corresponding to a fourth step of the training task. FIG. 17 may include a fifth training icon 1702 corresponding to a fifth step of the training task. FIG. 18 may include a sixth training icon 1802 corresponding to a sixth step of the training task. FIG. 19 may include a seventh training icon 1902 corresponding to a ninth step of the training task.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. For example, the software instructions may be executed to cause presentation of the training icon and initiate a training of the user to perform one or more actions corresponding to a training task based on a selection of the training task by the user. The software instructions can also be executed to provide a training icon that indicates a desired action of a user or illustrates a location of the desired action. The software instructions can also be executed to provide a title of the training task and/or a written description of the action. The software instructions can also be executed to receive a second user interaction and determine that, based on the second user interaction, that the user has completed a first action of the training task or has skipped the first action. The software instructions can also be executed to provide training icon(s) and/or written descriptions associated with further actions of the training task. The software instructions can also be executed to determine that a training task has been completed and indicate to the user that it has been completed. The software instructions and/or other executable code may be read from a computer readable storage medium (or mediums). The software instructions and/or other executable code may be read from a computer readable storage medium (or mediums).

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Implementation Considerations

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory. In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

One or more aspects or features of the subject matter disclosed or claimed herein (e.g., processes and methods) may be realized in digital electronic circuitry, integrated circuitry, specially designed application specific integrated circuits (ASICs), field programmable gate arrays (FPGAs) computer hardware, firmware, software, and/or combinations thereof. These various aspects or features may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server may be remote from each other and may interact through a communication network. The relationship of client and server arises by virtue of computer programs running on the respective computers and having a client-server relationship to each other.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium.

In some embodiments, to provide for interaction with a user, one or more aspects or features of the subject matter described herein may be implemented on a computer having a display device for displaying information to the user, and an input interface by which the user may provide input to the computer. Other kinds of devices may be used to provide for interaction with a user as well. Other possible input devices include touch screens or other touch-sensitive devices such as single or multi-point resistive or capacitive trackpads, voice recognition hardware and software, and the like.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways.

As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

The computer program product may include a computer readable storage medium (or mediums) having computer readable program instructions thereon for causing a processor to carry out aspects of the present disclosure. The computer readable storage medium can be a tangible device that can retain and store data and/or instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Computer readable program instructions, may as also referred to herein as, for example, "code," "instructions," "module," "application," "software application," and/or the like. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device.

Aspects of the present disclosure are described herein with reference to methods, apparatus (systems), and computer program products according to embodiments of the disclosure. It will be understood that each method can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks. Any of the above-mentioned processors, and/or devices incorporating any of the above-mentioned processors, may be referred to herein as, for example, "computers," "computer devices," "computing devices," "hardware computing devices," "hardware processors," "processing units," and/or the like.

It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

Example Embodiments

The following is provided as a list of certain non-limiting examples of various embodiments of the inventions described and illustrated herein. Some embodiments refer to other embodiments, adding additional features or characterizing features of the referred-to embodiments. Other embodiments are also possible.

1. A system comprising: a first non-transitory computer storage medium configured to store an image; a second non-transitory computer storage medium configured to at least store computer-executable instructions; and one or more computer hardware processors in communication with the second non-transitory computer storage medium, the one or more computer hardware processors configured to execute the computer-executable instructions to at least: cause display of the image on a user interface of a display device; cause display of a control icon on the user interface; receive a user interaction, wherein the user interaction corresponds to an interaction by a user with the first control icon, wherein the user interaction comprises a selection of a training task by the user; based at least in part on receiving the user interaction, determine a training task; and cause display of a training icon corresponding to a first action associated with the training task.

2. The system of embodiment 1, wherein the one or more computer hardware processors are further configured to execute the computer-executable instructions to: receive a second user interaction, wherein the second user interaction corresponds to a second interaction by the user with the training icon, wherein the second user interaction corresponds to the first action; determine that the user completed the first action based at least in part on receiving the second user interaction; and based at least in part on determining that the user completed the first action, cause display of a second training icon, the second training icon corresponding to a second action associated with the training task.

3. The system of embodiment 1, wherein the training task comprises one or more actions, the one or more actions including the first action.

4. The system of embodiment 1, wherein the one or more computer hardware processors are further configured to execute the computer-executable instructions to: cause display of a second image on the user interface; cause display of a second control icon on the user interface; receive a second user interaction, wherein the second user interaction corresponds to a second interaction by a user with the second control icon, wherein the second user interaction comprises a selection of a second training task by the user; based at least in part on receiving the second user interaction, determine a second training task; and cause display of a second training icon corresponding to a first action associated with the second training task.

5. The system of embodiment 4, wherein the second control icon and the control icon are different control icons.

6. The system of embodiment 4, wherein the second training task and the training task are different training tasks.

7. The system of embodiment 4, wherein the second image and the image are different images, wherein the second training task and the training task are a same training task.

8. The system of embodiment 1, wherein the image is an ultrasound image.

9. The system of embodiment 1, wherein the one or more computer hardware processors are further configured to execute the computer-executable instructions to cause display a title associated with the training task.

10. The system of embodiment 1, wherein the one or more computer hardware processors are further configured to execute the computer-executable instructions to cause display a title associated with the first action.

11. The system of embodiment 1, wherein the training task comprises a training to, one or more of: freeze the image; save the image; adjust a contrast of the image; adjust a time gain compensation; zoom; pan; draw an ellipse on the image; or change a scanning depth.

12. The system of embodiment 1, wherein causing display of the training icon comprises causing display of the training icon in a location associated with the first action.

13. The system of embodiment 1, wherein the training icon is an arrow.

14. The system of embodiment 1, wherein the training icon designates the first action.

15. The system of embodiment 1, wherein the training icon represents the first action.

16. The system of embodiment 1, wherein the one or more computer hardware processors are further configured to execute the computer-executable instructions to cause display of training text with the training icon, the training text designating a manner of executing the first action.

17. The system of embodiment 1, wherein one or more of the training icon or the control icon comprise a first color and the image comprises a second color.

18. The system of embodiment 1, wherein the one or more computer hardware processors are further configured to execute the computer-executable instructions to increase a size of one or more of the training icon or the control icon.

19. The system of embodiment 1, wherein the one or more computer hardware processors are further configured to execute the computer-executable instructions to receive a second user interaction, wherein the second user interaction corresponds to an interaction by the user with the training icon.

20. The system of embodiment 19, wherein the one or more computer hardware processors are further configured to execute the computer-executable instructions to, based at least in part on the second user interaction, determine that the first action is complete.

21. The system of embodiment 1, wherein the one or more computer hardware processors are further configured to execute the computer-executable instructions to receive a second user interaction, wherein the second user interaction corresponds to an interaction by the user with the image.

22. The system of embodiment 21, wherein the one or more computer hardware processors are further configured to execute the computer-executable instructions to, based at least in part on the second user interaction, determine that the first action is complete.

23. The system of embodiment 20 or 22, wherein the one or more computer hardware processors are further configured to execute the computer-executable instructions to, based at least in part on determining that the first action is complete, cause display of a second training icon.

24. The system of embodiment 20 or 22, wherein the one or more computer hardware processors are further configured to execute the computer-executable instructions to, based at least in part on determining that the first action is complete, modify the training icon to indicate that the first action is complete.

25. The system of embodiment 23, wherein the one or more computer hardware processors are further configured to execute the computer-executable instructions to cause display of a third training icon, wherein a user interaction with the third training icon causes display of the training icon.

26. The system of embodiment 25, wherein the third training icon comprises an arrow.

27. The system of embodiment 1, wherein the one or more computer hardware processors are further configured to execute the computer-executable instructions to determine that the first action is not complete.

28. The system of embodiment 27, wherein the one or more computer hardware processors are further configured to execute the computer-executable instructions to, based at least in part on determining that the first action is not complete, cause display of the training icon 29. The system of embodiment 27, wherein the one or more computer hardware processors are further configured to execute the computer-executable instructions to, based at least in part on determining that the first action is not complete, cause display of a prompt for the user to skip the first action.

30. The system of embodiment 27, wherein the one or more computer hardware processors are further configured to execute the computer-executable instructions to, based at least in part on determining that the first action is not complete, cause display of a prompt for the user to complete the first action.

31. The system of embodiment 1, wherein the training icon comprises one or more steps.

32. The system of embodiment 31, wherein the one or more computer hardware processors are further configured to execute the computer-executable instructions to cause display of an animation between the one or more steps.

33. The system of embodiment 1, wherein the one or more computer hardware processors are further configured to execute the computer-executable instructions to cause display of a training menu based at least in part on the user interaction, wherein the training menu includes a plurality of training tasks, the plurality of training tasks including the training task.

34. The system of embodiment 33, wherein the training menu includes a disablement option, wherein an interaction with the disablement option disables the training icon.

35. The system of embodiment 34, wherein the training menu includes a re-enablement option, wherein an interaction with the re-enablement option re-enables the training icon.

36. The system of embodiment 33, wherein to select the training task, the user interacts with the training menu.

37. The system of embodiment 1, wherein the one or more computer hardware processors are further configured to execute the computer-executable instructions to implement a computer application, wherein the display of the image is based at least in part on implementing the computer application.

38. The system of embodiment 37, wherein the computer application is one or more of a word processing application, a gaming application, a drafting application, an ultrasound imaging application, a simulation application, a product development application, a presentation application, an application suite, an engineering application, a multimedia application, or a spreadsheet application.

39. The system of embodiment 37, wherein the computer application is implemented locally or implemented via a network.

40. The system of embodiment 37, wherein the computer application is implemented via a system software.

41. A method of providing a system for training a user, the method comprising: causing display of an image on a user interface of a display device; causing display of a control icon on the user interface; receiving a user interaction, wherein the user interaction corresponds to an interaction by a user with the control icon, wherein the user interaction comprises a selection of a training task by the user; based at least in part on receiving the user interaction, determining a training task; and causing display of a training icon corresponding to a first action associated with the training task.

42. The method of embodiment 41, the method further comprising: receiving a second user interaction, wherein the second user interaction corresponds to a second interaction by the user with the training icon, wherein the second user interaction corresponds to the first action; determining that the user completed the first action based at least in part on receiving the second user interaction; and based at least in part on determining that the user completed the first action, causing display of a second training icon, the second training icon corresponding to a second action associated with the training task.

43. The method of embodiment 41, wherein the training task comprises one or more actions, the one or more actions including the first action.

44. The method of embodiment 41, the method further comprising: causing display of a second image on the user interface; causing display of a second control icon on the user interface; receiving a second user interaction, wherein the second user interaction corresponds to a second interaction by a user with the second control icon, wherein the second user interaction comprises a selection of a second training task by the user; based at least in part on receiving the second user interaction, determining a second training task; and causing display of a second training icon corresponding to a first action associated with the second training task.

45. The method of embodiment 44, wherein the second control icon and the control icon are different control icons.

46. The method of embodiment 44, wherein the second training task and the training task are different training tasks.

47. The method of embodiment 44, wherein the second image and the image are different images, wherein the second training task and the training task are a same training task.

48. The method of embodiment 41, wherein the image is an ultrasound image.

49. The method of embodiment 41, the method further comprising causing display of a title associated with the training task.

50. The method of embodiment 41, the method further comprising causing display of a title associated with the first action.

51. The method of embodiment 41, wherein the training task comprises a training to, one or more of: freeze the image; save the image; adjust a contrast of the image; adjust a time gain compensation; zoom; pan; draw an ellipse on the image; or change a scanning depth.

52. The method of embodiment 41, wherein causing display of the training icon comprises causing display of the training icon in a location associated with the first action.

53. The method of embodiment 41, wherein the training icon is an arrow.

54. The method of embodiment 41, wherein the training icon designates the first action.

55. The method of embodiment 41, wherein the training icon represents the first action.

56. The method of embodiment 41, the method further comprising causing display of training text with the training icon, the training text designating a manner of executing the first action.

57. The method of embodiment 41, wherein one or more of the training icon or the control icon are associated with a first color and the image is associated with a second color.

58. The method of embodiment 41, the method further comprising increasing a size of one or more of the training icon or the control icon.

59. The method of embodiment 41, the method further comprising receiving a second user interaction, wherein the second user interaction corresponds to an interaction by the user with the training icon.

60. The method of embodiment 59, the method further comprising, based at least in part on the second user interaction, determining that the first action is complete.

61. The method of embodiment 41, the method further comprising receiving a second user interaction, wherein the second user interaction corresponds to an interaction by the user with the image.

62. The method of embodiment 61, the method further comprising, based at least in part on the second user interaction, determining that the first action is complete.

63. The method of embodiment 60 or 62, the method further comprising, based at least in part on determining that the first action is complete, causing display of a second training icon.

64. The method of embodiment 60 or 62, the method further comprising, based at least in part on determining that the first action is complete, modifying the training icon to indicate that the first action is complete.
65. The method of embodiment 64, the method further comprising causing display of a third training icon, wherein a third user interaction with the third training icon causes display of the training icon.
66. The method of embodiment 65, wherein the third training icon comprises an arrow.
67. The method of embodiment 41, the method further comprising determining that the first action is not complete.
68. The method of embodiment 67, the method further comprising, based at least in part on determining that the first action is not complete, causing display of the training icon 69. The method of embodiment 67, the method further comprising, based at least in part on determining that the first action is not complete, causing display of a prompt for the user to skip the first action.
70. The method of embodiment 67, the method further comprising, based at least in part on determining that the first action is not complete, causing display of a prompt for the user to complete the first action.
71. The method of embodiment 41, wherein the training icon comprises one or more steps.
72. The method of embodiment 71, the method further comprising causing display of an animation between the one or more steps.
73. The method of embodiment 41, the method further comprising causing display of a training menu based at least in part on the user interaction, wherein the training menu includes a plurality of training tasks, the plurality of training tasks including the training task.
74. The method of embodiment 73, wherein the training menu includes a disablement option, wherein an interaction with the disablement option disables the training icon.
75. The method of embodiment 74, wherein the training menu includes a re-enablement option, wherein an interaction with the re-enablement option re-enables the training icon.
76. The method of embodiment 73, wherein to select the training task, the user selects the training task by interacting with the training menu.
77. The method of embodiment 41, the method further comprising implementing a computer application, wherein the display of the image is based at least in part on implementing the computer application.
78. The method of embodiment 77. wherein the computer application is one or more of a word processing application, a gaming application, a drafting application, an ultrasound imaging application, a simulation application, a product development application, a presentation application, an application suite, an engineering application, a multimedia application, or a spreadsheet application.
79. The method of embodiment 77, wherein the computer application is implemented locally or implemented via a network.
80. The method of embodiment 77, wherein the computer application is implemented via a system software.

The disclosed technology has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A system comprising:
   a first non-transitory computer storage medium configured to store an image;
   a second non-transitory computer storage medium configured to at least store computer-executable instructions; and
   one or more computer hardware processors in communication with the second non-transitory computer storage medium, the one or more computer hardware processors configured to execute the computer-executable instructions to at least:
      cause display of an ultrasound image on a user interface of a display device;
      cause display of a control icon on the user interface;
      receive a user interaction corresponding to an interaction by a user with the control icon, wherein the interaction causes generation and presentation of a plurality of selectable tasks on the user interface, each task corresponding to a process performed using the user interface;
      receive on the user interface a user selection of a displayed task; and
      cause display of a series of training icons corresponding to a series of actions associated with the selected task, wherein causing display of each training icon in the series comprises display of each training icon in a location on the user interface associated with the corresponding action, and wherein the location of the training icons is configured to guide the user to the location of each corresponding action.

2. The system of claim 1, wherein the one or more computer hardware processors are further configured to execute the computer-executable instructions to generate and cause display of training text on the user interface with the series of training icons, the training text designating a manner of executing the first action.

3. The system of claim 2, wherein the one or more computer hardware processors are further configured to execute the computer-executable instructions to cause display of an animation of the series of training icons from a first location on the user interface to a second location on the user interface, the second location on the user interface near where a next action is needed to be performed by the user.

4. The system of claim 1, wherein the one or more computer hardware processors are further configured to execute the computer-executable instructions to:
   receive a second user interaction, wherein the second user interaction corresponds to a second interaction by the user with one of the training icons, wherein the second user interaction corresponds to the first action;
   determine that the user completed the first action based at least in part on receiving the second user interaction; and
   based at least in part on determining that the user completed the first action, cause display of a second training icon, the second training icon corresponding to a second action associated with the training task.

5. The system of claim 1, wherein the one or more computer hardware processors are further configured to execute the computer-executable instructions to:
   cause display of a second ultrasound image on the user interface;

cause display of a second control icon on the user interface;
receive a second user interaction, wherein the second user interaction corresponds to a second interaction by a user with the second control icon, wherein the second user interaction comprises a selection of a second training task by the user;
based at least in part on receiving the second user interaction, determine a second training task; and
cause display of a second training icon corresponding to a first action associated with the second training task.

6. The system of claim 5, wherein the second control icon and the control icon are different control icons.

7. The system of claim 5, wherein the second training task and the training task are different training tasks.

8. The system of claim 5, wherein the second ultrasound image and the ultrasound image are different images, wherein the second training task and the training task are a same training task.

9. The system of claim 1, wherein the training task comprises a training to, one or more of:
freeze the ultrasound image;
save the ultrasound image;
adjust a contrast of the ultrasound image;
adjust a time gain compensation;
zoom;
pan;
draw an ellipse on the ultrasound image; or change a scanning depth.

10. The system of claim 1, wherein one or more of the training icon or the control icon comprise a first color and the ultrasound image comprises a second color.

11. The system of claim 1, wherein the one or more computer hardware processors are further configured to execute the computer-executable instructions to
receive a second user interaction, wherein the second user interaction corresponds to an interaction by the user with one of the series of training icons or corresponds to an interaction by the user with the ultrasound image;
based at least in part on the second user interaction, determine that the first action is complete; and
modify the one of the series of training icons to indicate that the first action is complete.

12. The system of claim 11, wherein the one or more computer hardware processors are further configured to execute the computer-executable instructions to, based at least in part on determining that the first action is complete, cause display of a second training icon.

13. The system of claim 12, wherein the one or more computer hardware processors are further configured to execute the computer-executable instructions to cause display of a third training icon, wherein an interaction with the second training icon causes display of the third training icon.

14. The system of claim 13, wherein one or more of the training icon, the second training icon, or the third training icon include sequential information identifying an order of the training icon, the second training icon, and the third training icon.

15. The system of claim 1, wherein the one or more computer hardware processors are further configured to execute the computer-executable instructions to determine that the first action is not complete, and based at least in part on determining that the first action is not complete, cause display of a prompt for the user to complete the first action.

16. A method of providing a system for training a user, the method comprising:
generating and presenting an ultrasound image on a user interface of a display device;
generating and presenting a control icon on the user interface;
receiving a user interaction corresponding to an interaction by a user with the control icon, wherein the interaction causes generation and presentation of a plurality of selectable tasks on the user interface, each task corresponding to a process performed using the user interface;
receiving on the user interface a user selection of a displayed task; and
generating and presenting of a series of training icons corresponding to a first action associated with the selected task, wherein causing display of the series of training icons comprises causing display of each icon in the series of training icons in a location on the user interface associated with the first action, and
wherein the location of the training icons is configured to guide the user to the location of each corresponding action,
wherein the method is performed by one or more computer hardware processors configured to execute computer-executable instructions stored on a non-transitory computer readable medium.

17. The method of claim 16, further comprising generating and presenting training text with the series of training icons on the user interface, the training text designating a manner of executing the first action.

18. The method of claim 17, further comprising generating and presenting an animation of the series of training icons from a first location on the user interface to a second location on the user interface, the second location on the user interface near where a next action is needed to be performed by the user.

19. The method of claim 16, further comprising:
receiving a second user interaction via the user interface, wherein the second user interaction corresponds to a second interaction by the user with one of the series of training icons, wherein the second user interaction corresponds to the first action;
determining that the user completed the first action based at least in part on receiving the second user interaction; and
based at least in part on determining that the user completed the first action, generating and presenting a second training icon on the user interface, the second training icon corresponding to a second action associated with the training task.

20. The method of claim 16, further comprising:
generating and presenting a second ultrasound image on the user interface;
generating and presenting a second control icon on the user interface;
receiving a second user interaction via the user interface, wherein the second user interaction corresponds to a second interaction by a user with the second control icon;
based at least in part on receiving the second user interaction, determining a second training task; and
generating and presenting a second training icon corresponding to a first action associated with the second training task.

* * * * *